United States Patent
Otake et al.

(10) Patent No.: US 11,199,596 B2
(45) Date of Patent: Dec. 14, 2021

(54) ARRAY COIL AND MAGNETIC RESONANCE IMAGING APPARATUS

(71) Applicant: HITACHI, LTD., Tokyo (JP)

(72) Inventors: Yosuke Otake, Tokyo (JP); Kohjiro Iwasawa, Tokyo (JP); Masayoshi Dohata, Tokyo (JP); Hisaaki Ochi, Tokyo (JP); Takahide Shimoda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/757,444

(22) PCT Filed: Aug. 23, 2018

(86) PCT No.: PCT/JP2018/031204
§ 371 (c)(1),
(2) Date: Apr. 20, 2020

(87) PCT Pub. No.: WO2019/087541
PCT Pub. Date: May 9, 2019

(65) Prior Publication Data
US 2021/0072331 A1    Mar. 11, 2021

(30) Foreign Application Priority Data
Nov. 1, 2017   (JP) .............................. JP2017-211959

(51) Int. Cl.
*G01R 33/34* (2006.01)
*G01R 33/3415* (2006.01)
(Continued)

(52) U.S. Cl.
CPC ... *G01R 33/34092* (2013.01); *G01R 33/3415* (2013.01); *G01R 33/3642* (2013.01); *G01R 33/3806* (2013.01)

(58) Field of Classification Search
CPC ............ G01R 33/3415; G01R 33/3642; G01R 33/3806; G01R 33/34092
See application file for complete search history.

(56) References Cited

U.S. PATENT DOCUMENTS 5,144,240 A * 9/1992 Mehdizadeh .... G01R 33/34046
324/318
7,026,818 B2 * 4/2006 Machida ............ G01R 33/3415
324/309
(Continued)

FOREIGN PATENT DOCUMENTS

JP       2680235 B2    11/1997
JP    2009-22483 A     2/2009
(Continued)

OTHER PUBLICATIONS

International Preliminary Report on Patentability received in corresponding International Application No. PCT/JP2018/031204 dated May 5, 2020.

(Continued)

*Primary Examiner* — Dixomara Vargas
(74) *Attorney, Agent, or Firm* — Mattingly & Malur, PC

(57) ABSTRACT

A high-frequency array coil for an MRI apparatus includes: a plurality of coil units each of which includes a plurality of RF reception coils including a conductor loop and adjusted to receive a magnetic resonance signal; an extension conductor which includes a part of each conductor loop of each RF reception coil of the plurality of coil units and a conductor connecting the parts; and an extension conductor control circuit which adjusts a reception frequency of the extension conductor. The extension conductor is disposed so as to be wound in a spiral shape when the extension conductor is disposed on a subject and a direction of a magnetic field to be detected intersects a direction of a magnetic field detected by the RF reception coil constituting (Continued)

the coil unit. Accordingly, the detection efficiency of an RF coil can be increased and an image with a high SNR can be obtained.

14 Claims, 19 Drawing Sheets

(51) Int. Cl.
*G01R 33/36* (2006.01)
*G01R 33/38* (2006.01)

(56) References Cited

U.S. PATENT DOCUMENTS

| | | | | |
|---|---|---|---|---|
| 7,119,541 B2* | 10/2006 | Barberi | G01R 33/34046 | |
| | | | | 324/318 |
| 7,176,689 B2* | 2/2007 | Machida | G01R 33/3415 | |
| | | | | 324/318 |
| 7,999,548 B1* | 8/2011 | Brown | G01R 33/3678 | |
| | | | | 324/318 |
| 8,035,383 B2 | 10/2011 | Ochi et al. | | |
| 8,089,280 B2* | 1/2012 | Soutome | G01R 33/3678 | |
| | | | | 324/318 |
| 8,497,682 B2* | 7/2013 | Huish | G01R 33/3415 | |
| | | | | 324/318 |
| 9,541,614 B2* | 1/2017 | Soutome | G01R 33/34 | |
| 10,222,433 B2* | 3/2019 | Leussler | G01R 33/36 | |
| 10,267,874 B2* | 4/2019 | Tomiha | G01R 33/3692 | |
| 10,653,335 B2* | 5/2020 | Dohata | G01R 33/34084 | |
| 2003/0132750 A1* | 7/2003 | Machida | G01R 33/3664 | |
| | | | | 324/322 |
| 2005/0156598 A1* | 7/2005 | Matschl | G01R 33/3664 | |
| | | | | 324/322 |
| 2006/0012370 A1* | 1/2006 | Barberi | G01R 33/34046 | |
| | | | | 324/318 |
| 2006/0087320 A1* | 4/2006 | Machida | G01R 33/3664 | |
| | | | | 324/322 |
| 2007/0285096 A1* | 12/2007 | Soutome | G01R 33/34069 | |
| | | | | 324/318 |
| 2008/0061785 A1* | 3/2008 | Soutome | G01R 33/3628 | |
| | | | | 324/319 |
| 2008/0197848 A1* | 8/2008 | Zhai | G01R 33/3664 | |
| | | | | 324/318 |
| 2009/0160441 A1 | 6/2009 | Dohata et al. | | |
| 2010/0253351 A1* | 10/2010 | Huish | G01R 33/3692 | |
| | | | | 324/318 |
| 2012/0306494 A1 | 12/2012 | Yang et al. | | |
| 2013/0015720 A1* | 1/2013 | Shimokawa | H02J 7/025 | |
| | | | | 307/104 |
| 2013/0069652 A1* | 3/2013 | Otake | G01R 33/3664 | |
| | | | | 324/322 |
| 2013/0241556 A1 | 9/2013 | Bollenbeck et al. | | |
| 2013/0314091 A1* | 11/2013 | Otake | G01R 33/3657 | |
| | | | | 324/322 |
| 2015/0054506 A1* | 2/2015 | Eberler | G01R 33/36 | |
| | | | | 324/309 |
| 2016/0033598 A1* | 2/2016 | Hamamura | G01R 33/3642 | |
| | | | | 324/307 |
| 2016/0135711 A1* | 5/2016 | Dohata | G01R 33/3664 | |
| | | | | 600/422 |
| 2016/0356867 A1* | 12/2016 | Fujita | G01R 33/3642 | |
| 2017/0123024 A1* | 5/2017 | Li | G01R 33/3628 | |
| 2017/0254864 A1* | 9/2017 | Otake | G01R 33/3635 | |
| 2017/0307701 A1* | 10/2017 | Leussler | G01R 33/422 | |
| 2019/0310331 A1* | 10/2019 | Otake | G01R 33/34076 | |
| 2019/0383891 A1* | 12/2019 | Iwasawa | G01R 33/34084 | |
| 2020/0041587 A1* | 2/2020 | Findeklkee | G01R 33/3664 | |
| 2020/0278405 A1* | 9/2020 | Yang | G01R 33/3685 | |
| 2020/0292642 A1* | 9/2020 | Yang | G01R 33/3678 | |

FOREIGN PATENT DOCUMENTS

| | | |
|---|---|---|
| JP | 4733177 B2 | 7/2011 |
| WO | 2007/129429 A1 | 11/2007 |

OTHER PUBLICATIONS

International Search Report of PCT/JP2018/031204 dated Oct. 16, 2018.

* cited by examiner (a)

(b)

(a)

(b)

(a)

(b)

(c)

(a)

(b)

(a)

(b)

(a)

(b)

(c)

(a)

(b)

(a)

(b)

(a)

(a)

(a) 700

(b)

ARRAY COIL AND MAGNETIC RESONANCE IMAGING APPARATUS

TECHNICAL FIELD

The present invention relates to a magnetic resonance imaging (MRI) apparatus, and more particularly, to an RF coil that irradiates a high-frequency magnetic field (RF magnetic field) to detect a nuclear magnetic resonance signal.

BACKGROUND ART

An MRI apparatus is an apparatus that images an arbitrary cross-section across a subject using a nuclear magnetic resonance phenomenon. Specifically, the MRI apparatus irradiates a subject placed in a spatially uniform magnetic field (static magnetic field) with an RF magnetic field so as to cause nuclear magnetic resonance, detects a generated nuclear magnetic resonance signal, and performs image processing on the detected signal so as to acquire a cross-section image.

A device which irradiates the subject with the RF magnetic field or detects the nuclear magnetic resonance signal generated from the subject is called a Radio Frequency (RF) coil. The RF coil includes a loop portion (a coil loop) which irradiates and detects the RF magnetic field. When the coil loop becomes smaller, a sensitivity area becomes narrower, but sensitivity becomes higher. Meanwhile, when the coil loop becomes larger, the sensitivity area becomes wider. In this way, in the RF coil, there is a trade-off between the high sensitivity and the width of the sensitivity area. In order to achieve both high sensitivity and a wide sensitivity area, there is a multi-channel array coil in which a plurality of small-diameter loop RF coils having high sensitivity are arranged in an array. Since the multi-channel array coil has high sensitivity and a wide sensitivity area, an image with a high Signal to Noise Ratio (SNR) can be obtained.

Incidentally, since the nuclear magnetic resonance signal is a signal of a rotating magnetic field generated in a direction perpendicular to the static magnetic field generated by the magnet, it is preferable that the RF coil is disposed in a direction in which a magnetic field perpendicular to the static magnetic field can be irradiated and detected. Generally, since a loop coil (surface coil) can detect and irradiate a magnetic field in a direction perpendicular to a surface of a coil, signal detection efficiency is highest when a coil surface and the axis of the static magnetic field have a parallel relationship.

However, in a vertical magnetic field type MRI apparatus in which a magnet generating a static magnetic field is divided vertically in order to enhance a sense of openness, when small-diameter RF coils are arranged to cover a subject, a coil surface is not parallel to a direction of a static magnetic field in many positions compared with a tunnel type horizontal magnetic field type. Thus, there was a problem in that signal detection efficiency was poor.

In contrast, Patent Document 1 discloses a technology of preparing an RF coil using a relatively large loop (hereinafter, referred to as a solenoid coil) covering a subject once and a plurality of small-diameter RF coils, arranging these coils so that magnetic fields generated by them are orthogonal to each other, and realizing high sensitivity on a surface of the subject and high sensitivity in a deep portion of the subject.

Further, Patent Document 2 discloses a technology of arranging a plurality of relatively large loop coils covering a subject once, arranging these coils so that magnetic fields generated by them are orthogonal to each other, realizing high sensitivity in a deep portion of a subject, and enabling high-speed imaging with the plurality of arranged coils.

CITATION LIST

Patent Document

Patent Document 1: Japanese Patent No. 2680235
Patent Document 1: Japanese Patent No. 4733177

SUMMARY OF THE INVENTION

Technical Problem

In recent years, high-speed imaging using a difference in spatial sensitivity between sub-coils of a multi-channel array coil has become widespread. High-speed imaging can be accelerated as the number of channels increases. Also, the image quality of high-speed imaging improves as the signal detection efficiency of the sub-coil becomes better and the difference in sensitivity distribution becomes larger. Thus, in order to realize high-quality and high-speed imaging, it is necessary to increase the number of channels of the coil and to improve the signal detection efficiency of each sub-coil constituting the RF coil.

However, as disclosed in Patent Document 1 or Patent Document 2 in which the solenoid coils are arranged and the RF coils are further arranged so that the magnetic field generated by the coil is orthogonal to the magnetic field generated by the RF coil, since the orthogonal direction is limited, it is difficult to increase the number of channels and to obtain high sensitivity by further increasing the number of channels. Further, as disclosed in Patent Document 1 or Patent Document 2, the RF coil using the solenoid coil disposed in a direction perpendicular to a body axis direction of the subject is limited in application to the vertical magnetic field type MRI apparatus. As a result, there are limitations in application.

The invention has been made in view of the above-described circumstances and an object of the invention is to provide an array coil enabling multi-channels and having high signal detection efficiency and high sensitivity.

Solution to Problem

In order to solve the above-described problems, the invention provides a high-frequency array coil in which a plurality of RF reception coils are arranged so as not to be magnetically coupled to each other, an extension conductor is formed by connecting a part of conductor loops of the RF reception coils along the arrangement of the RF reception coils, and an extension conductor control circuit is provided so that the extension conductor functions as an RF reception coil.

That is, an aspect of the invention provides a high-frequency array coil including: a plurality of coil units each of which includes a plurality of RF reception coils including a conductor loop and adjusted to receive a magnetic resonance signal; an extension conductor which includes a part of each conductor loop of each RF reception coil of the plurality of coil units and a conductor connecting the parts; and an extension conductor control circuit which adjusts a reception frequency of the extension conductor.

Another aspect of the invention provides a magnetic resonance imaging apparatus including: a static magnetic field generating magnet which generates a static magnetic field in a vertical direction; a gradient magnetic field generating coil which applies a magnetic field gradient to the static magnetic field; and a high-frequency coil which generates a high-frequency magnetic field in a space of a static magnetic field generated by the static magnetic field generating magnet or detects the high-frequency magnetic field, wherein the high-frequency array coil is used as the high-frequency coil.

Advantageous Effects of the Invention

According to the invention, in an array coil in which small-diameter RF reception coils are arranged, a high-sensitivity image can be obtained by simulating a large current loop.

BRIEF DESCRIPTION OF THE DRAWINGS

FIG. 1(a) is an external view of a horizontal magnetic field type MRI apparatus and FIG. 1(b) is an external view of an open vertical magnetic field type MRI apparatus.

FIG. 7(a) is a diagram illustrating an arrangement with respect to a subject and FIG. 7(b) is a diagram illustrating an arrangement of an overlapping portion of the array coil.

DETAILED DESCRIPTION OF EMBODIMENTS

Figure 1:
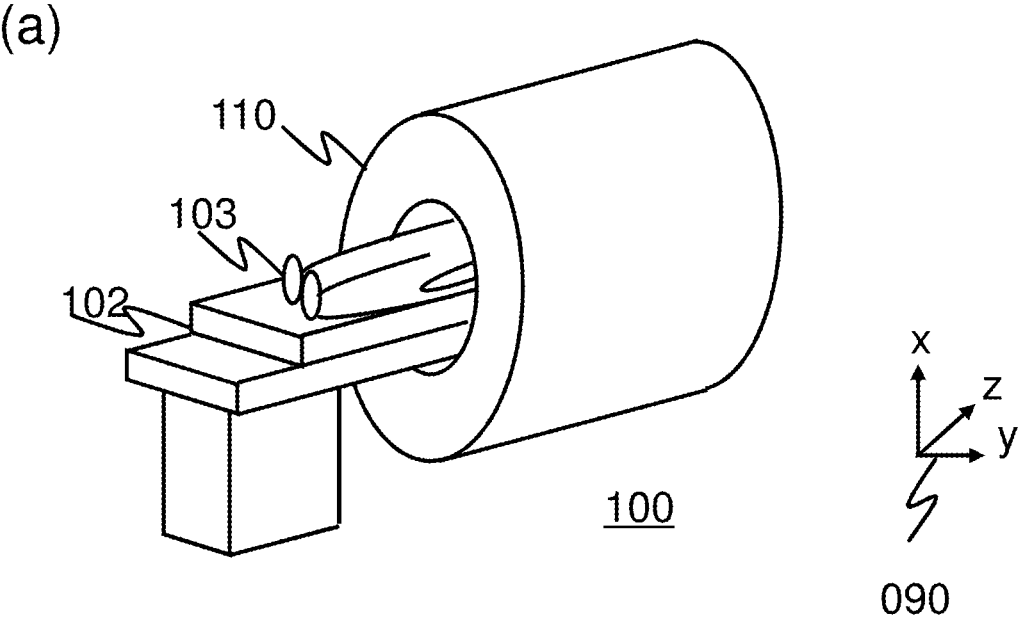
FIG. 1 is an external view of an MRI apparatus according to an embodiment of the invention, where
Figure 1:
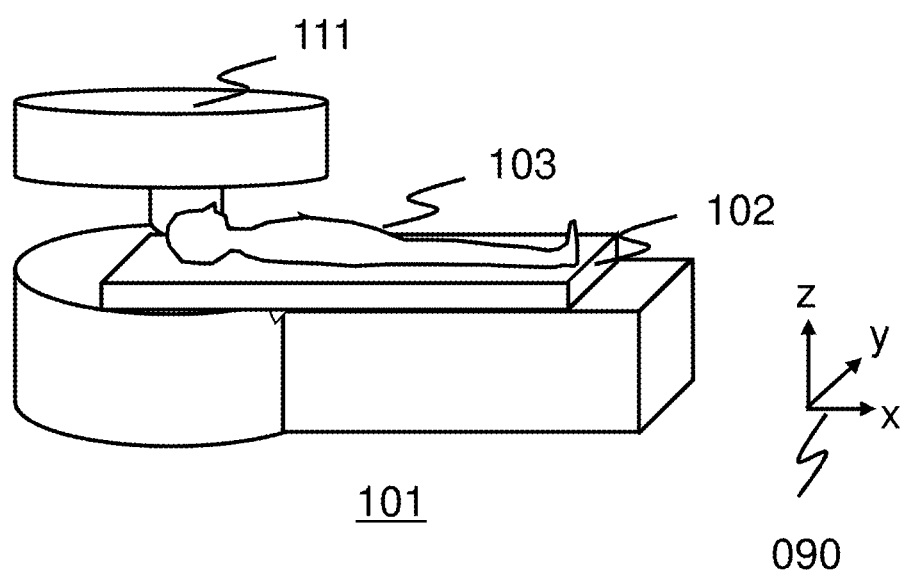

Hereinafter, an embodiment of an array coil of the invention and an MRI apparatus using the same will be described with reference to the drawings. In the drawings according to the following embodiments, the same components are denoted by the same reference numerals, and a repetitive description thereof will be omitted.

Prior to the embodiment of the array coil of this embodiment, an embodiment of the MRI apparatus that adopts the array coil of this embodiment will be described.

<<Embodiment of MRI Apparatus>>

FIG. 1 illustrates an appearance of the MRI apparatus according to this embodiment. FIG. 1(a) illustrates a horizontal magnetic field type MRI apparatus 100 that uses a tunnel type magnet 110 generating a static magnetic field by a solenoid coil. FIG. 1(b) illustrates an open vertical magnetic field type MRI apparatus 101 in which a magnet 111 is vertically separated in order to enhance a sense of openness. In a coordinate system 090 of the drawing, a direction of a static magnetic field is denoted by z and a direction orthogonal to that direction is denoted by x and y (the same applies below). These MRI apparatuses 100 and 101 include a table 102 on which an inspection target (a subject) 103 is placed. The subject 103 placed on the table is disposed in an inspection space in which a uniform magnetic field (a static magnetic field) is generated by the magnets 110 and 111. In the horizontal magnetic field type, the body axis direction of the subject 103 matches the static magnetic field direction and in the vertical magnetic field type, the body axis direction is orthogonal to the static magnetic field direction.

The array coil of this embodiment can be applied without being limited to a specific magnetic field type. Hereinafter, the details of the MRI apparatus will be described by exemplifying the vertical magnetic field type MRI apparatus.

Figure 2:
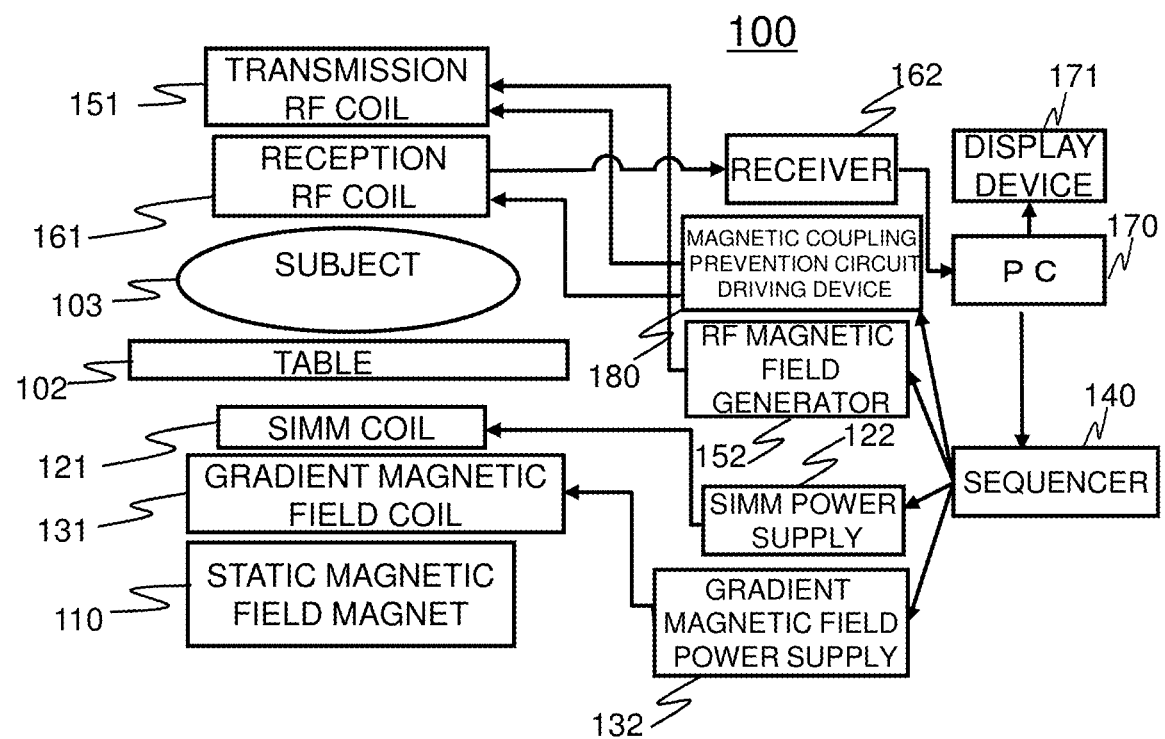
FIG. 2 is a block diagram illustrating a schematic configuration of the MRI apparatus.

The MRI apparatus 100 includes, as illustrated in FIG. 2, a vertical magnetic field type magnet (a static magnetic field magnet) 110, a gradient magnetic field coil 131, a transmission RF coil 151, a reception RF coil 161, a gradient magnetic field power supply 132, a SIMM coil 121, a SIMM power supply 122, an RF magnetic field generator 152, a receiver 162, a magnetic coupling prevention circuit driving device 180, a computer (PC) 170, a sequencer 140, and a display device 171. Additionally, the inspection target (the subject) 103 placed on the table 102 is inserted into a static magnetic field space (an imaging space) formed by the static magnetic field magnet 110.

The gradient magnetic field coil 131 is connected to the gradient magnetic field power supply 132 and generates a gradient magnetic field. The gradient magnetic field coil 131 and the gradient magnetic field power supply 132 constitute a gradient magnetic field forming unit forming a gradient magnetic field. The SIMM coil 121 is connected to the SIMM power supply 122 and adjusts the uniformity of the magnetic field. The transmission RF coil 151 is connected to the RF magnetic field generator 152 and irradiates (transmits) an RF magnetic field to the subject 103.

The reception RF coil 161 is connected to the receiver 162 and receives a nuclear magnetic resonance signal from the subject 103. Here, a multi-channel RF coil (hereinafter, referred to as an array coil) including a plurality of RF coils and a conductor loop is adopted as the reception RF coil 161 according to this embodiment. In the description below, it is assumed that the number of the RF coils constituting the array coil and the number of channels are the same. The array coil which is the reception RF coil 161 will be described below in detail.

The magnetic coupling prevention circuit driving device 180 is connected to a circuit (a magnetic coupling prevention circuit) which is connected to each of the transmission RF coil 151 and the reception RF coil 161 and prevents the magnetic coupling between the transmission RF coil 151 and the reception RF coil 161.

The sequencer 140 sends a command to the gradient magnetic field power supply 132, the RF magnetic field generator 152, and the magnetic coupling prevention circuit driving device 180 to operate them. The command is sent according to an instruction of the computer (PC) 170. Further, the sequencer 140 sets a magnetic resonance frequency as a reference for detection by the receiver 162 according to an instruction from the computer (PC) 170. For example, the subject 103 is irradiated with the RF magnetic field through the transmission RF coil 151 according to the command from the sequencer 140. A nuclear magnetic resonance signal generated from the subject 103 by the irradiation of the RF magnetic field is detected by the reception RF coil 161 and is detected by the receiver 162.

The computer (PC) 170 controls the operation of the entire MRI apparatus 100 and performs various signal processes. For example, a signal detected by the receiver 162 is received via an A/D conversion circuit and a signal process such as image reconstruction (a function of an image reconstruction unit) is performed. The result is displayed on the display device 171. Detected signals and measurement conditions are stored in a storage medium as necessary. Further, the sequencer 140 is caused to send a command so that each device is operated at a pre-programmed timing and intensity. Further, when there is a need to adjust the static magnetic field uniformity, the sequencer 140 sends a command to the SIMM power supply 122 so as to adjust the magnetic field uniformity in the SIMM coil 121.

<Outline of Transmission RF Coil and Reception RF Coil>

As described above, the MRI apparatus of this embodiment uses two kinds of RF coils of the transmission RF coil 151 and the reception RF coil 161. In the transmission RF coil 151 and the reception RF coil 161, one RF coil can serve as both of them and an individual RF coil can be used.

Hereinafter, the detail of the RF coil will be described by exemplifying a case in which the transmission RF coil 151 and the reception RF coil 161 are separate RF coils, the transmission RF coil 151 has an umbrella-shaped RF coil (flat birdcage RF coil), and the reception RF coil 161 is a multi-channel array coil including a plurality of RF coils.

First, the arrangement of an umbrella-shaped RF coil 300 used as the transmission RF coil 151 and the array coil 400 used as the reception RF coil 161 and the connection mode of the umbrella-shaped RF coil 300, the array coil 400, the RF magnetic field generator 152, the receiver 162, and the magnetic coupling prevention circuit driving device 180 will be described with reference to FIG. 3.

Figure 3:
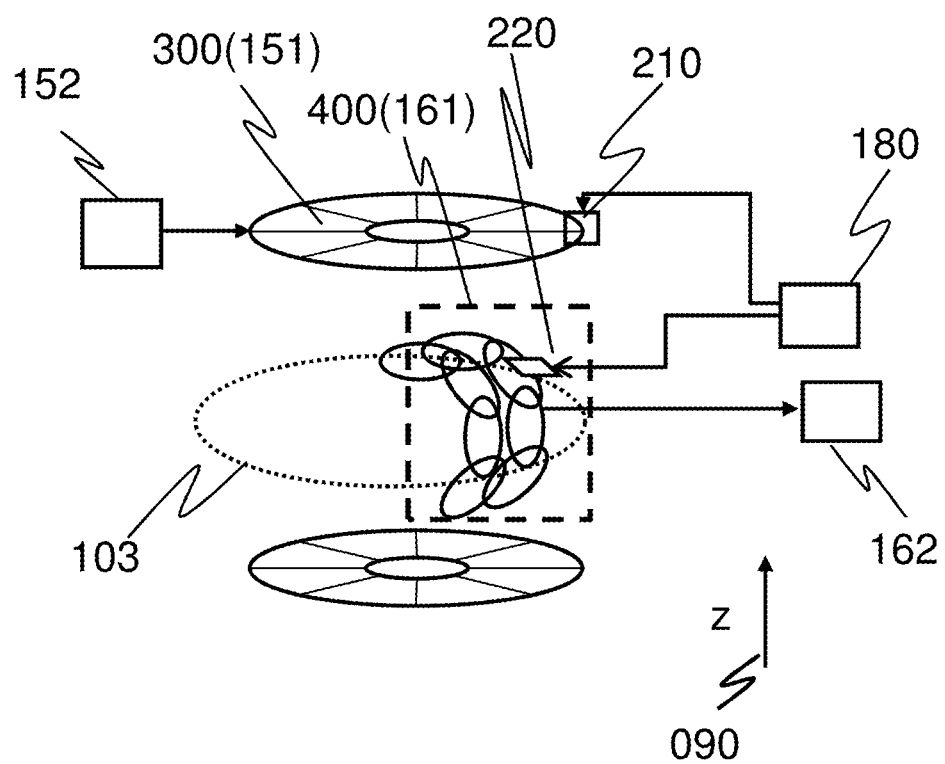
FIG. 3 is an explanatory diagram illustrating a connection between a transmission RF coil and a reception RF coil of the MRI apparatus according to the embodiment of the invention.

As illustrated in FIG. 3, the umbrella-shaped RF coil 300 includes two disks, each disk has an umbrella shape (including an elliptical column and a polygonal column) including two circular conductors and a plurality of linear conductors connecting them, and the axis of the disk is disposed coaxially with the center axis (the axis of the Z direction) of the magnet 110. The subject 103 is disposed at the inside of the umbrella-shaped RF coil 300. Then, the array coil 400 is disposed adjacently inside the umbrella-shaped RF coil 300 so as to cover the subject 103. Further, as described above, the umbrella-shaped RF coil 300 is connected to the RF magnetic field generator 152. The array coil 400 is connected to the receiver 162.

Further, the umbrella-shaped RF coil 300 is provided with a magnetic coupling prevention circuit 210 which prevents the magnetic coupling with the array coil 400 and the array coil 400 is provided with a magnetic coupling prevention circuit 220 which prevents the magnetic coupling with the umbrella-shaped RF coil 300. These are called a transmission/reception magnetic coupling prevention circuit. Due to the transmission/reception magnetic coupling prevention circuit, it is possible to transmit the RF magnetic field and to receive the nuclear magnetic resonance signal without magnetic coupling therebetween in the above-described arrangement.

[Transmission RF Coil]

Figure 4:
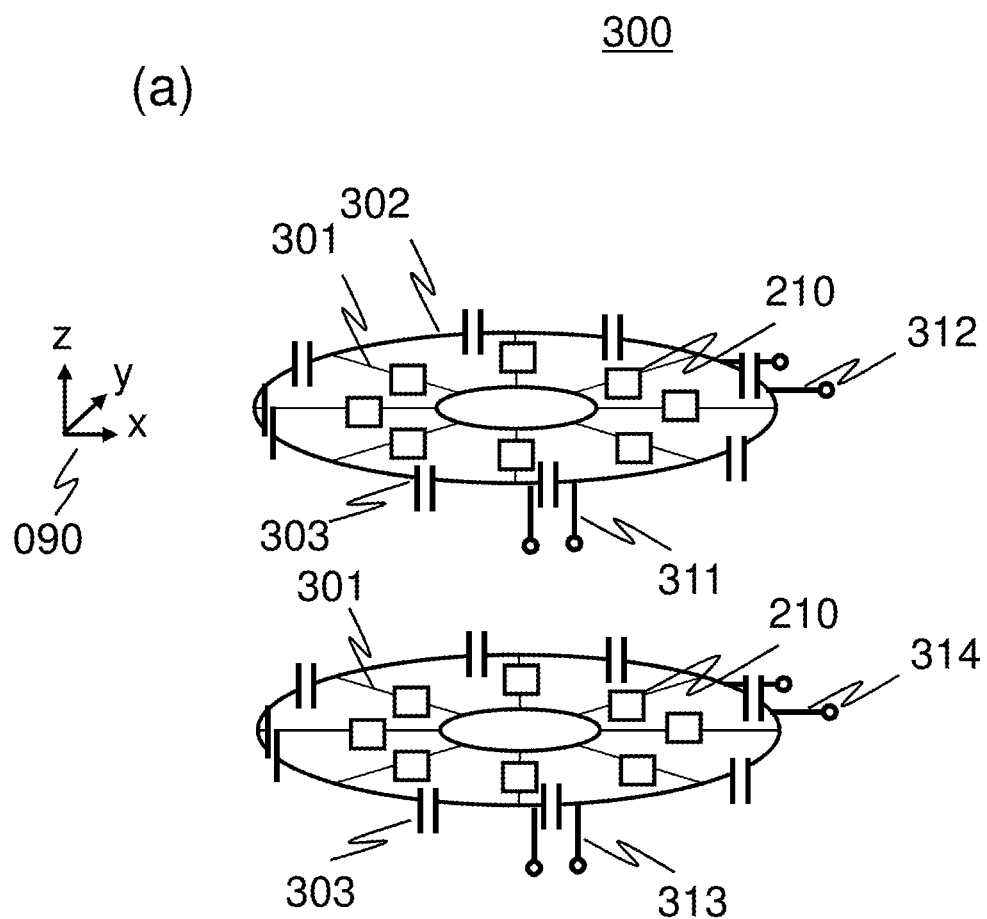
FIG. 4(a) is a diagram illustrating a configuration of an umbrella-shaped RF coil used as a transmission RF coil and FIG. 4(b) is a diagram illustrating an example of a transmission/reception magnetic coupling prevention circuit of the transmission RF coil.
Figure 4:
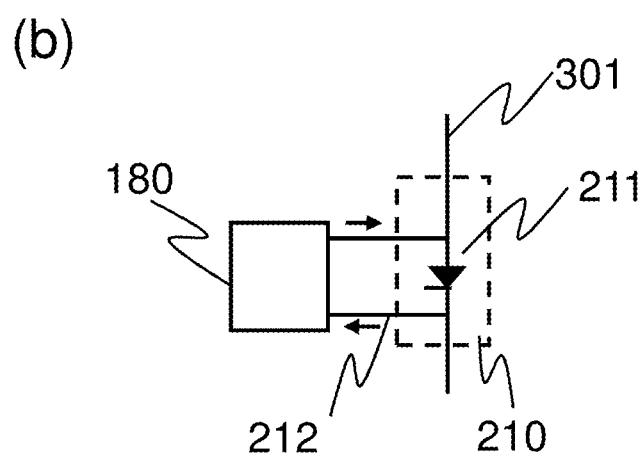

Next, the umbrella-shaped RF coil 300 which is used as the transmission RF coil 151 of this embodiment will be described with reference to FIG. 4.

The umbrella-shaped RF coil 300 of this embodiment is adjusted so that the resonance frequency (magnetic resonance frequency) of the element to be excited becomes a resonance frequency and irradiates the RF magnetic field at the magnetic resonance frequency. In this embodiment, the magnetic resonance frequency is adjusted to the magnetic resonance frequency f0 of the hydrogen nucleus, which can excite the hydrogen nucleus. Hereinafter, the magnetic resonance frequency of the irradiated RF magnetic field is set to f0.

FIG. 4(a) is a block diagram illustrating a configuration of the umbrella-shaped RF coil 300 of this embodiment. As illustrated in this drawing, each of two umbrella-shaped RF coils 300 of this embodiment includes a plurality of linear conductors 301, a circular conductor 302 which connects the ends of the linear conductors 301, and a capacitor 303 which is inserted into the circular conductor 302.

Further, the umbrella-shaped RF coil 300 includes four input ports 311, 312, 313, and 314. Transmission signals respectively having different phases of 0°, 90°, 180°, and 270° are input to the first input port 311, the second input port 312, the third input port 313, and the fourth input port 314 and the RF magnetic field is efficiently applied to the subject 103.

Further, in the umbrella-shaped RF coil 300 of this embodiment, the transmission/reception magnetic coupling prevention circuit 210 for preventing the magnetic coupling in the reception RF coil 161 (the array coil 400) is inserted in series to the linear conductor 301 of the umbrella-shaped RF coil 300.

For example, as illustrated in FIG. 4(b), the transmission/reception magnetic coupling prevention circuit 210 can be configured as a PIN diode 211 inserted in series to the linear conductor 301 and a control signal line 212 is connected to both ends thereof. The control signal line 212 is connected to the magnetic coupling prevention circuit driving device 180. It is preferable to insert a choke coil (not illustrated) to the control signal line 212 in order to prevent the mixing of the high frequency.

The PIN diode 211 has a characteristic that the diode normally has a high resistance (OFF) and becomes substantially conductive (ON) when the value of the direct current flowing in the forward direction of the PIN diode 211 exceeds a certain value. In this embodiment, the ON/OFF of the PIN diode 211 is controlled by the direct current output from the magnetic coupling prevention circuit driving device 180 using this characteristic. That is, when transmitting and receiving a high-frequency signal, a control current is caused to flow through the control signal line 212 so that the PIN diode 211 becomes a conductive state, the umbrella-shaped RF coil 300 functions as the transmission RF coil 151. Further, when receiving a nuclear magnetic resonance signal, the flow of the control current is stopped so that the umbrella-shaped RF coil 300 has high impedance and is in an open state.

In this way, in this embodiment, since the direct current (the control current) flowing from the magnetic coupling prevention circuit driving device 180 is controlled, the umbrella-shaped RF coil 300 is caused to function as the transmission RF coil 151 when transmitting and receiving the high-frequency signal and the umbrella-shaped RF coil in an open state eliminates the magnetic coupling with the array coil 400 which is the reception RF coil 161 in an open state when receiving the nuclear magnetic resonance signal.

[Reception RF Coil]

Next, the array coil 400 which is used as the reception RF coil 161 in the MRI apparatus of this embodiment will be described with reference to FIG. 5. The array coil 400 includes a plurality of coil units, a linear conductor which functions as a coil, and a control circuit which adjusts the linear conductor. Each coil unit includes one or a plurality of sub-coils. The linear conductor is a conductor portion (hereinafter, referred to as an extension conductor) which extends by connecting apart of the conductors of the plurality of sub-coils constituting the array coil 400 and the linear conductor itself also functions as the RF coil. In the array coil 400 of this embodiment, an adjustment circuit (an extension conductor control circuit) for adjusting the resonance frequency of the extension conductor is inserted between the coil unit and the coil unit. Further, a part of the circuit element for adjusting the resonance frequency of each sub-coil on the extension conductor may also serve as the extension conductor control circuit.

The coil unit of this embodiment may be a coil unit in which at least one or more sub-coils are arranged, but FIG. 5(a) illustrates an array coil obtained by sequentially connecting a first coil unit 401 including three sub-coils, an extension conductor control circuit 403, and a second coil unit 402 including three sub-coils as an example. The extension conductor is a linear conductor portion that connects a part of each of the coil loops of the sub-coils arranged on the left and right in the figure from the extension conductor control circuit 403.

Here, three sub-coils 410 constituting the first coil unit 401 are respectively referred to as a sub-coil 410A, a sub-coil 410B, and a sub-coil 410C and three sub-coils 410 constituting the second coil unit 402 are respectively referred to as a sub-coil 410D, a sub-coil 410E, and a sub-coil 410F. However, when it is not necessary to particularly distinguish the components of each sub-coil 410 constituting the array coil 400 for each sub-coil 410, the last letter of the symbol is omitted (the same applies below).

Each of six sub-coils 410 is a surface coil having a loop arranged and configured to cover a subject on a substantially plane and the magnetic coupling between the sub-coils 410 in the array coil is prevented by a decoupling capacitor which shares one capacitor 425 and is one of magnetic coupling prevention means.

Each sub-coil 410 functions as one channel while being adjusted so as to receive a nuclear magnetic resonance signal of an element to be excited by the umbrella-shaped RF coil 300. Signals which are received by the sub-coil 410A to the sub-coil 410F are respectively sent to the receiver 162.

Since six sub-coils 410 have the same configuration, the configuration of the sub-coil 410A will be described representatively below. The sub-coil 410A includes a loop coil unit 420A which includes a conductor loop detecting a nuclear magnetic resonance signal (an RF magnetic field), a low input impedance preamplifier 430A, and an inductor 441A which connects the loop coil unit 420A and the low input impedance preamplifier 430A and is connected to the receiver 162 via the low input impedance preamplifier 430A.

One terminal on the side of the loop coil unit 420A in the low input impedance preamplifier 430A is connected to one end of a parallel capacitor 424A of the loop coil unit 420A via the inductor 441A. The other terminal on the side of the loop coil unit 420A in the low input impedance preamplifier 430A is directly connected to the other end of the parallel capacitor 424A of the loop coil unit 420A.

The inductor 441A may be replaced by a capacitor under the influence of the inductance of the conductor connecting the parts. When the low input impedance preamplifier is viewed from the loop coil unit 420A, the impedance of the parallel resonance circuit including the capacitor 424A, the low input impedance preamplifier 430A, the inductor 441A or a substitute capacitor, and a conductor connecting them is set to be higher than the impedances of other frequencies at f0. Accordingly, the magnetic coupling is prevented. Specifically, the magnetic coupling with the sub-coil 410A hardly occurs when viewed from the sub-coil other than the sub-coil 410A.

A loop portion of the loop coil unit 420A is configured as a conductor 41A. Then, the loop coil unit 420A includes the capacitor 424A which is inserted in series to the inductor component and constitutes the parallel resonance circuit by the inductor component and the capacitor 424A. The capacitor 424A is called a parallel capacitor in order to be distinguished from other capacitors.

Further, a capacitor 422A adjusting a resonance frequency and the transmission/reception magnetic coupling prevention circuit 220 are inserted in series to the loop coil unit 420A. The capacitor 422A is called a series capacitor in order to be distinguished from other capacitors. Here, a case in which one series capacitor 422A is provided is exemplified, but a plurality of series capacitors may be provided or, this capacitor may be omitted if the adjustment can be performed with the length of the conductor 41A or other capacitors.

Further, in the loop coil unit 420A, a capacitor 426A for adjusting the resonance frequency of the sub-coil 410A and the resonance frequency of the extension conductor is inserted in series to the conductor 41A. Further, the capacitor 425 is inserted in series to the loop coil unit 420A in order to eliminate the magnetic coupling with the loop coil unit 420B. Then, the loop coil unit 420B is also configured to share the capacitor 425. The capacitor 425 is called a decoupling capacitor in order to be distinguished from other capacitors.

In this way, the sub-coil 410A includes the inductor 441A which is an adjustment circuit element, the series capacitor 422A which is inserted in series to the inductor component of the loop coil unit 420A, the parallel capacitor 424A which is inserted in series to the inductor component and allows the loop coil unit 420A to be the parallel resonance circuit, the decoupling capacitor 425 which is inserted in series to the inductor component and eliminates the magnetic coupling with the adjacent coil, and the extension conductor frequency adjustment capacitor 426A which is inserted in series to the inductor component and adjusts the resonance frequency of the extension conductor.

The sub-coil 410B and the sub-coil 410C also have the same configuration as that of the sub-coil 410A. Further, the sub-coil 410D, the sub-coil 410E, and the sub-coil 410F constituting the second coil unit 402 also have the same configuration.

In addition to the adjustment component such as the capacitor, the transmission/reception magnetic coupling prevention circuit 220 is inserted in series to the loop coil unit 420 of each sub-coil 410. The transmission/reception magnetic coupling prevention circuit 220 eliminates the magnetic coupling with the umbrella-shaped RF coil 300 which is the transmission RF coil 151. For example, as illustrated in FIG. 5(b), the transmission/reception magnetic coupling prevention circuit 220 can include a capacitor 423 which is inserted in series to a conductor 41 constituting the loop of the loop coil unit 420, a PIN diode 221 which is connected in parallel to the capacitor 423, and an inductor 222.

A control signal line 223 is connected to both ends of the PIN diode 221. Then, the control signal line 223 is connected to the magnetic coupling prevention circuit driving device 180. It is preferable to insert a choke coil (not illustrated) to the control signal line 223 in order to prevent the mixing of the high frequency. The inductor 222 and the capacitor 423 are adjusted so as to resonate in parallel at the frequency of the received nuclear magnetic resonance signal.

In general, the parallel resonance circuit has a characteristic that the circuit has higher impedance (higher resistance) than other frequencies at the resonance frequency. Thus, when a current flows to the PIN diode 221, the PIN diode 221 is turned on and the capacitor 423 of the loop 421 resonates in parallel together with the inductor 222 at the frequency of the received nuclear magnetic resonance signal so as to become a high impedance state. Thus, a part of the loop coil unit 420 has high impedance and is in an open state at the frequency of the received nuclear magnetic resonance signal and the RF coil 410 including the loop coil unit 420 is also in an open state.

In this way, when a current flows to the PIN diode 221 so that the diode is turned on, the magnetic coupling between each sub-coil 410 and the umbrella-shaped RF coil 300 is eliminated. Therefore, the magnetic coupling between the array coil 400 having each sub-coil 410 as a coil element and the umbrella-shaped RF coil 300 is also eliminated. FIG. 5(a) illustrates an example in which one transmission/reception magnetic coupling prevention circuit 220 is inserted into the sub-coil 410, but the number of the transmission/reception magnetic coupling prevention circuits 220 inserted into the sub-coil 410 is not limited to one. Two or more circuits may be inserted into each loop 421. By inserting a plurality of circuits, the magnetic coupling between the transmission RF coil 151 and the reception RF coil 161 can be sufficiently reduced.

Further, the configuration of the transmission/reception magnetic coupling prevention circuit 220 other than the extension conductor control circuit 403 is not limited to the above-described configuration. For example, as in a modified example of a transmission/reception magnetic coupling prevention circuit 220m illustrated in FIG. 5(c), a cross diode 221m may be used instead of the PIN diode 221. Accordingly, when a large signal flows to the conductor 41 constituting the loop 421, the cross diode 221m is turned on and the capacitor 423 inserted into the conductor 21 resonates in parallel together with the inductor 222 at the frequency of the received nuclear magnetic resonance signal so as to become a high impedance state. In this case, the magnetic coupling prevention circuit driving device 180 may not be provided.

Next, the extension conductor will be described with reference to FIG. 6. As described above, each sub-coil 410 constituting the array coil 400 includes a parallel resonance circuit including a capacitor 424, a low input impedance preamplifier 430, and an inductor 441 and the parallel resonance frequency is adjusted to the same frequency as the magnetic resonance frequency fo. For this reason, the parallel resonance circuit has high impedance and is in an open state. When viewed from the extension conductor control circuit 403, each of the coil units 401 and 402 is equivalent to the circuit illustrated in FIG. 6. The linear conductor which extends so as to share a part of the conductor and the sub-coils disposed on both sides with the extension conductor control circuit 403 interposed therebetween is an extension conductor 405.

Here, the extension conductor control circuit 403 includes a conductor which connects a conductor 41C of the sub-coil 410C of the coil unit 401 and a conductor 41D of the RF coil 410D of the coil unit 402, a capacitor 403-1 which is inserted in series into the conductor, and a transmission/reception magnetic coupling prevention circuit 450. The transmission/reception magnetic coupling prevention circuit 450 is a circuit that prevents magnetic coupling by an external signal similarly to the transmission/reception magnetic coupling prevention circuit 220 inserted into the loop coil portion 420 of each sub-coil 410 and can adopt a configuration illustrated in FIG. 5(b) or FIG. 5(c).

Figure 5:
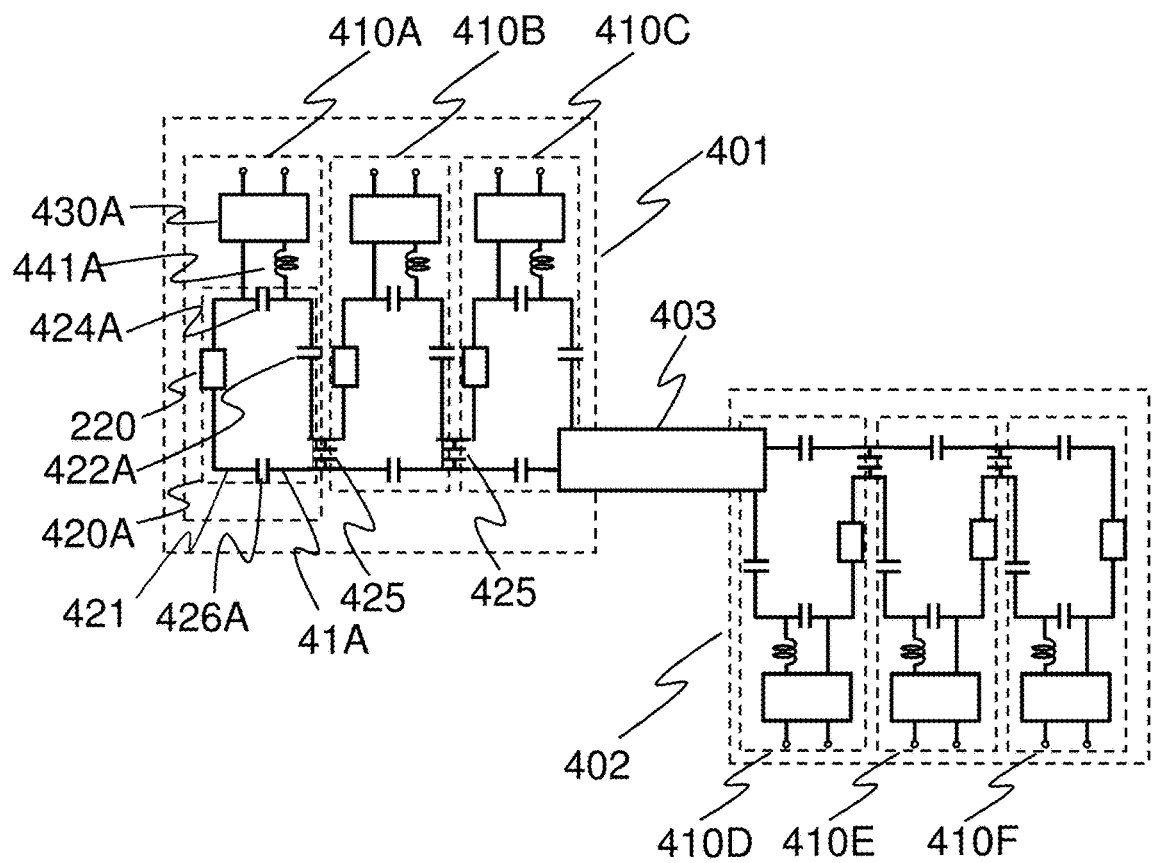
FIG. 5(a) is a diagram illustrating an embodiment of an array coil used as a reception RF coil and FIGS. 5(b) and 5(c) are diagrams illustrating an example of a transmission/reception magnetic coupling prevention circuit of the reception RF coil.
Figure 5:
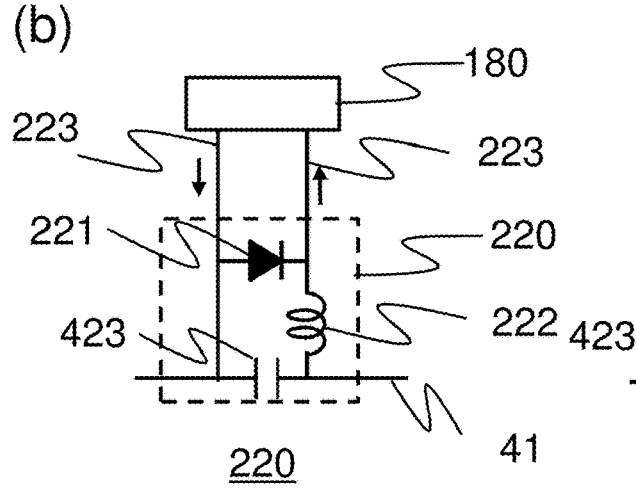
Figure 5:
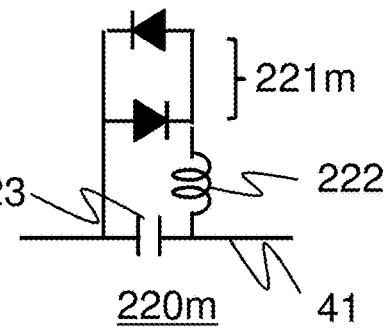
Figure 6:
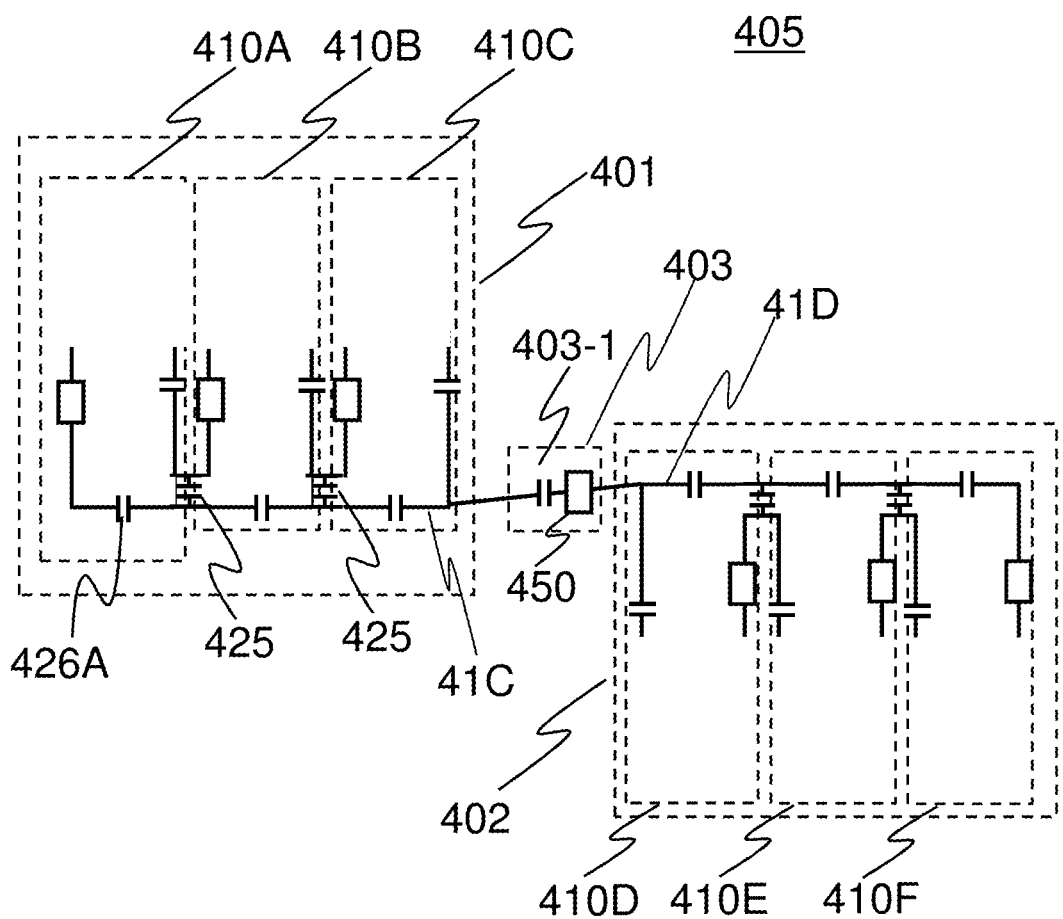
FIG. 6 is an explanatory diagram illustrating an operation and an effect of the array coil of FIG. 5(a).

Further, in the example illustrated in FIGS. 5 and 6, the extension conductor control circuit 403 is inserted between two adjacent coil units, but may be inserted between any of the sub-coils 410A to 410F. The capacitor 403-1 is a circuit element that adjusts the resonance frequency of the extension conductor 405 together with the capacitor 426 independently from the resonance frequency of each sub-coil.

In the array coil 400 of this embodiment, since the values of the inductance or the capacitance of the adjustment circuit element included in each of the sub-coils 410A to 410F and the inductance or the capacitance caused by the extension conductor control circuit 403 are adjusted, the array coil is disposed and adjusted so that the sub-coils 410A to 410F respectively receive the nuclear magnetic resonance signal and the extension conductor 405 also receives the nuclear magnetic resonance signal.

Figure 7:
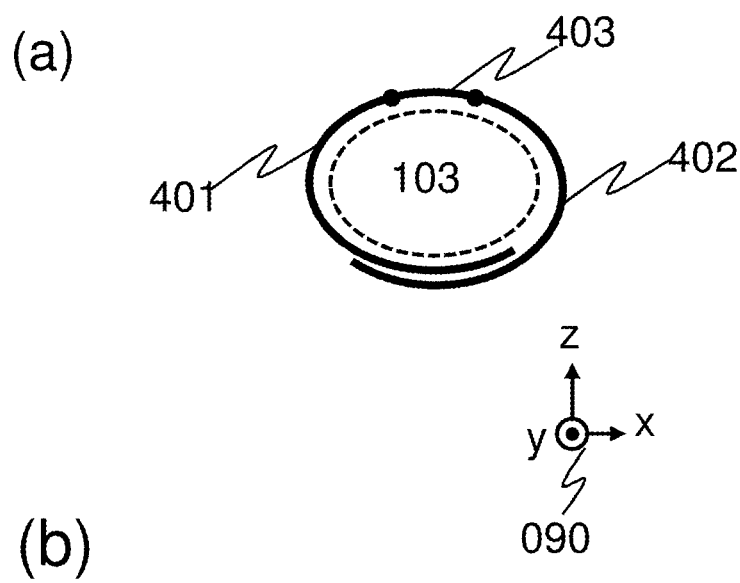
FIG. 7 is a diagram illustrating an arrangement of the array coil of FIG. 5(a), where
Figure 7:
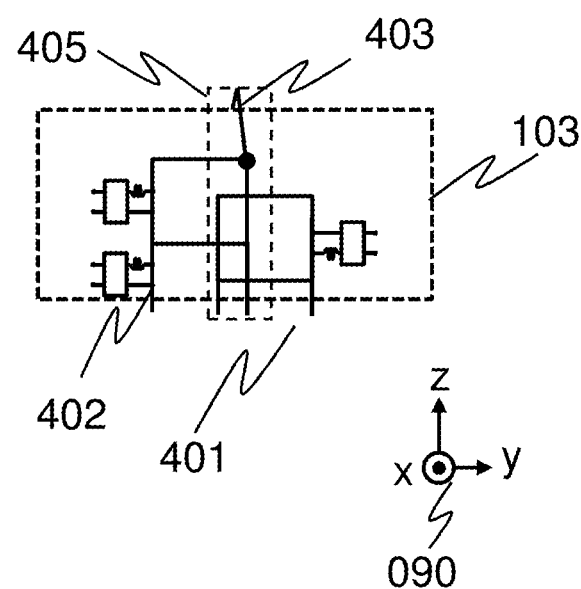

For the arrangement, for example, the extension conductor 405 including the first coil unit 401, the extension conductor control circuit 403, and the second coil unit 402 is disposed so as to cover a subject in a spiral shape of one or more turns so that a magnetic field can be generated in a direction substantially orthogonal to the static magnetic field direction. At this time, this arrangement can eliminate the magnetic coupling of the sub-coils constituting each coil unit. In an example illustrated in FIG. 5 in which the coil units 401 and 402 are disposed on both sides with the extension conductor 405 interposed therebetween, as illustrated in FIG. 7(*a*), both side surfaces of the subject 103 are covered by the sub-coils of the coil units 401 and 402 and hence the extension conductor 405 is disposed so as to cover the subject 103. Accordingly, the direction of the main magnetic field formed by the extension conductor 405 becomes a direction perpendicular to the static magnetic field and hence the magnetic resonance signal can be detected. The main magnetic field direction indicates a direction of a strong magnetic field about the center portion of the coil (loop conductor or spiral conductor). In the case of the loop coil, a direction perpendicular to the coil surface becomes the main magnetic field direction. Further, the positions of both ends of the extension conductor 405 are displaced in the y direction. In this case, as illustrated in FIG. 7(*b*), the sub-coils on both side surfaces are arranged so as to be displaced in the y direction and to partially overlap each other. Accordingly, it is possible to prevent the magnetic coupling between the sub-coils having overlapping positions.

Regarding the direction of the current, the sub-coil 410A and the extension conductor 405 are arranged and adjusted so as to resonate at the same time when receiving a signal and the sub-coil 410A and the spirally wound extension conductor 405 are adjusted so that a current loop flows like a figure of 8. Similarly, each of the sub-coils 410B to 410F is also adjusted such that a current loop flows like a figure of 8 between each of the sub-coils 410B to the sub-coils 410F and the extension conductor 405. That is, a difference between the phase of the current flowing through the extension conductor 405 and the phase of the current flowing through the loop coil portion 420 of the sub-coil 410 is adjusted to be smaller than 90°.

Next, a case in which the sensitivity is improved by arranging and adjusting the sub-coils as described above will be described.

In general, as illustrated in Equation (1), the strength S of the signal detected by the RF coil of the MRI apparatus, that is, the strength S of the signal to be output is obtained by integrating the inner product of the magnetic field B generated by the RF coil and the nuclear magnetization Mxy generated in the direction perpendicular to the static magnetic field with the volume V of the subject.

[Math. 1]

$$S = -\frac{\partial}{\partial t}\int \vec{B} \cdot \vec{M}_{xy} dV \tag{1}$$

[Math. 2]

$$\vec{M}_{xy} = M_{xy}(\cos \omega t - \sin \omega t) \tag{2}$$

Here, t indicates time and ω indicates the angular velocity of the rotating magnetic field.

As understood from the equations (1) and (2), when the magnetic field generated by the RF coil matches the direction of nuclear magnetization, a large signal, that is, high sensitivity is obtained. That is, high sensitivity can be obtained by arranging the RF coil so that a large magnetic field is generated on the XY plane.

In the array coil 400 of this embodiment, the fact that the coil arranged on the XY plane can generate a magnetic field on the XY plane and obtain high depth sensitivity will be described with reference to FIG. 8. Here, for the simple description, the third sub-coil 410C with the lowest signal detection efficiency and the lowest sensitivity, in which the coil surface is arranged at a position perpendicular to the Z axis, will be described as an example. Further, the description will be made with the operation at the time of power supply on the basis of the reciprocity theorem that the operation and sensitivity at the time of reception of the RF coil are the same as the operation and sensitivity at the time of power supply to the coil.

Figure 8:
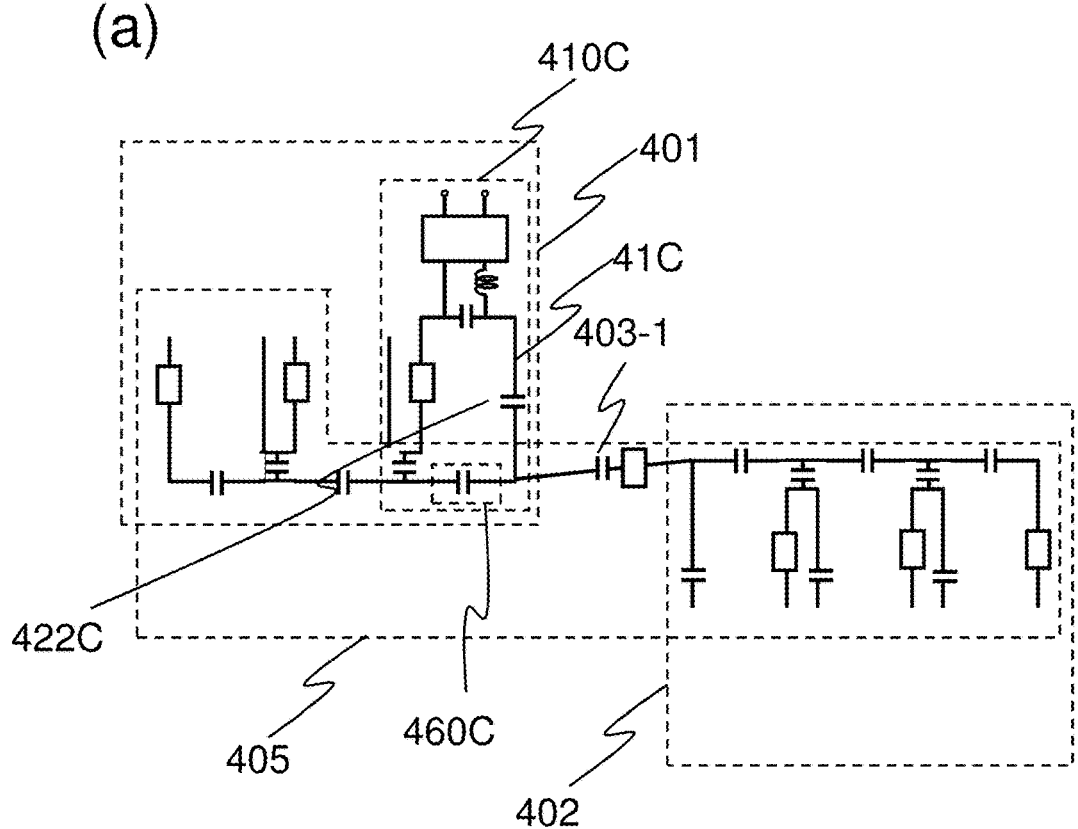
FIGS. 8(a) and 8(b) are explanatory diagrams illustrating an operation and an effect of the array coil of FIG. 5(a).
Figure 8:
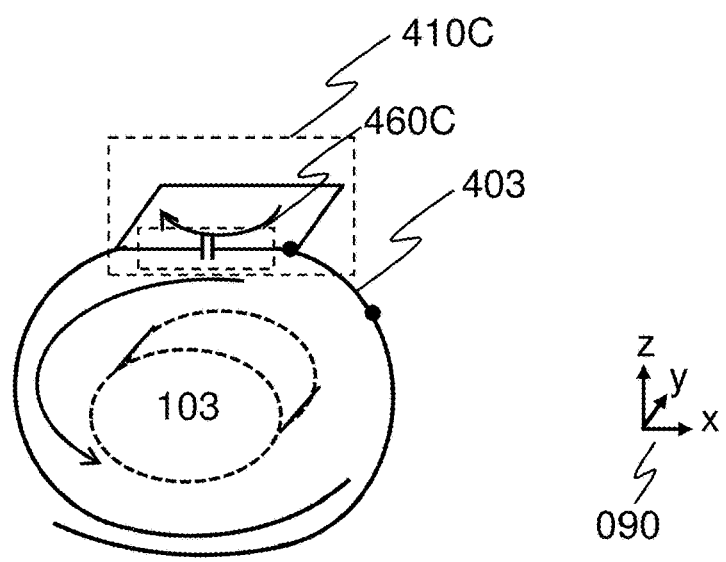

FIG. 8(*a*) illustrates a substantial circuit when power is supplied to the sub-coil 410C of this embodiment. Since the sub-coil other than the sub-coil 410C is configured so that the impedance of the parallel resonance circuit including the capacitor 424, the low input impedance preamplifier, the inductor 441 or the substitute capacitor, and the conductor connecting them is set to be higher than the impedances of other frequencies at f0, the sub-coil has a high impedance and the loop conductor in an open state. For that reason, when power is supplied to the sub-coil 410C, the sub-coil 410C has a circuit in which the linear conductor, that is, the extension conductor 405 is connected to the sub-coil 410C as illustrated in FIG. 8(*b*). When power is supplied to the circuit, a current flows basically through the conductor 41C of the sub-coil 410C. Accordingly, a potential difference occurs in a portion 460C which is shared by the extension conductor 405 and the conductor 41C of the sub-coil 410C. At this time, since the extension conductor has a substantially dipole antenna shape when viewed from the common portion 460C, the conductor can be regarded as a dipole antenna. Further, since the extension conductor is also adjusted so as to resonate at the same frequency, the extension conductor 405 is also supplied with power secondarily from the portion sharing the conductor with the conductor 41C (hereinafter, secondary power supply) and a current also flows through the extension conductor.

In the dipole antenna, one terminal has a positive potential and the other terminal has a negative potential when viewed from the power supply point and the electric field is high at the ends. When the extension conductor is disposed in a spiral shape as in this embodiment, since the plus end and the minus end are adjacent to each other, a potential difference occurs and hence electric field coupling occurs. As a result, the extension conductor disposed in a spiral shape causes a loop-shaped current through the electric field coupling and generates the same magnetic field as the loop coil.

As described above, the extension conductor has a spiral shape of one or more turns and is disposed so as to cover the subject. That is, since the extension conductor is disposed on the XZ plane, the extension conductor can generate a large magnetic field in the Y direction. Further, since the conductor is disposed so as to cover the subject, high depth sensitivity can be obtained.

As described above, since power is also supplied to the extension conductor via the loop coil unit 420C of the sub-coil 410C, even a coil arranged on the XY plane can achieve high depth sensitivity.

In the description above, the third sub-coil 410C has been exemplified, but also in the first sub-coil 410A, the second sub-coil 410B, and the fourth sub-coil 410D to the sixth sub-coil 410F, a part of the conductor is operated with the extension conductor to obtain high depth sensitivity. Accordingly, even when the sub-coil 410A to the sub-coil 410F are arranged on any of the cylindrical surfaces around the Y direction, the efficiency of the sub-coil near the inefficient XY plane is increased. As a result, high sensitivity can be realized as an array coil.

The imaging method using the MRI apparatus of this embodiment has the same operation as the MRI apparatus of the related art and the subject 103 disposed in the static magnetic field space generated by the static magnetic field magnet 110 is applied with the RF magnetic field pulse from the transmission RF coil 151 (for example, the umbrella-shaped RF coil 300) and the gradient magnetic pulse from the gradient magnetic field coil 131 according to, for example, a pulse sequence selected by the imaging method.

During the operation of the transmission RF coil 151, the reception RF coil 161 eliminates the magnetic coupling with the reception RF coil 161 while the transmission/reception magnetic coupling prevention circuit 220 is opened. After a predetermined time elapses from the application of the RF magnetic field pulse, a nuclear magnetic resonance signal generated from an atomic nucleus of an element constituting the living tissue of the subject 103 is received by the reception RF coil 161 (multi-channel coil: array coil 400) disposed close to the subject 103. During the receiving operation, the transmission/reception magnetic coupling prevention circuit 210 is opened and the magnetic coupling between the transmission RF coil 151 and the reception RF coil 161 is eliminated.

The computer (signal processing unit) 170 processes MR signals respectively received by the RF coil of the reception RF coil 161 and creates an image of the subject by an image reconstruction method according to a parallel imaging algorithm, for example, when the imaging method is a high-speed imaging method using parallel imaging. Alternatively, images obtained by the signals of the respective channels are MAC-combined to create images. At this time, sensitivity distribution information of each RF coil is appropriately used.

According to the MRI apparatus of this embodiment, since the multi-channel coil (the array coil 400) which is specifically disposed and adjusted is used as the reception RF coil 161, the detection efficiency of each RF coil is increased and hence a high-quality image can be obtained in a wide range.

Furthermore, the MRI apparatus according to this embodiment has a feature that the specifically adjusted reception RF coil is used and the other configurations can be modified variously. For example, this embodiment includes that a part of the embodiments illustrated in FIG. 2 are omitted or a component not illustrated in FIG. 2 is added. Further, in the above-described embodiment, the vertical magnetic field type MRI apparatus has been described, but the horizontal magnetic field type MRI apparatus can be also applied in the same way.

<<Embodiment of Array Coil>>

Next, an embodiment of the array coil of the invention will be described.

The array coil of this embodiment is applied to a so-called multi-channel RF coil including a plurality of RF coils and a conductor loop and includes a plurality of coil units which includes a plurality of RF reception coils (sub-coils) each including a conductor loop and adjusted to receive a magnetic resonance signal, an extension conductor which is obtained by electrically connecting a part of each conductor loop of each RF reception coil of the plurality of coil units, and an extension conductor control circuit which adjusts a reception frequency of the extension conductor. The extension conductor is disposed so as to form a spiral shape of one or more turns in the arrangement on the subject and is adjusted to receive a nuclear magnetic resonance signal. The array coil according to this embodiment can be applied without being limited to the direction of the static magnetic field and is disposed so as to generate and detect a magnetic field in a direction orthogonal to the direction of the static magnetic field. In the array coil of the embodiment, the number of coil units and the number of sub-coils constituting the coil unit are increased and the number of channels can be increased.

Hereinafter, a detailed embodiment of the array coil will be described. Additionally, the array coil 400 which is described as the reception RF coil in the embodiment of the MRI apparatus is one embodiment of the array coil of the invention and the configuration or arrangement will be described in detail by using this embodiment as a first embodiment. In the other embodiments, the configuration or arrangement different from that of the first embodiment will be mainly described.

First Embodiment

Figure 9:
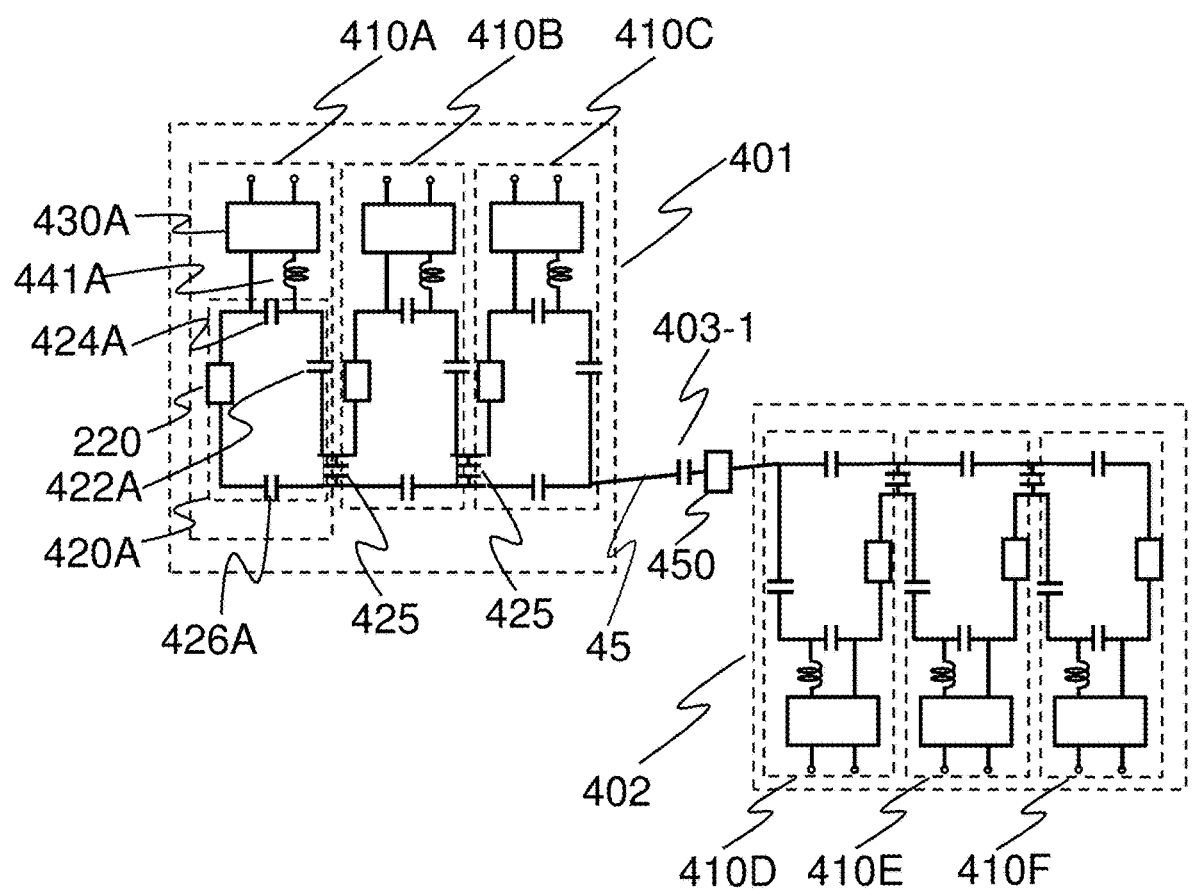
FIG. 9 is a diagram illustrating an array coil of a first embodiment.

As illustrated in FIG. 9, the array coil according to this embodiment includes the first coil unit 401 which includes three RF coils (sub-coils), the extension conductor control circuit 403 into which the capacitor 403-1 is inserted in series, and the second coil unit 402 and these components are connected in this order. Further, when viewed from the XZ plane, as illustrated in FIG. 7(a), these are disposed so as to cover the subject at least once. When viewed from the YZ plane, as illustrated in FIG. 7(b), the extension conductor 405 is disposed in a spiral shape.

A coordinate system 090 illustrated in FIG. 7(b) is set such that a longitudinal direction of the drawing is the Z-axis direction, the horizontal direction is the Y-axis direction, and a direction perpendicular to the drawing is the X direction. That is, the axis of the spiral extension conductor is disposed in the Y-axis direction. The spiral shape is not limited to a circular shape illustrated in the drawing, but may be an elliptical shape or a polygonal shape.

In each of the sub-coils 410A to 410F of the coil unit of this embodiment, the magnetic coupling is eliminated by a decoupling means using the capacitor 425 in order to eliminate the magnetic coupling with the adjacent sub-coil. Further, each sub-coil is adjusted to the same frequency as the magnetic resonance frequency f0 so as to receive the magnetic resonance signal. The sub-coil 410C of the first coil unit 401 and the sub-coil 410D of the second coil unit 402 are connected by the linear conductor 45 into which the capacitor 403-1 is inserted and the conductor of a part of the first coil unit 401, the conductor of a part of the second coil unit 402, and the linear conductor 45 constitute the extension conductor 405.

As illustrated in FIG. 6, the extension conductor 405 of this embodiment indicates a path extending from the sub-coil 410A to the transmission/reception magnetic coupling prevention circuit 220 through the linear conductor 45 without passing through the parallel capacitor 424 of the sub-coil 410F.

When receiving a signal of each of the RF coils 410, a current flows through the extension conductor 405 at the same time so as to form a loop current and the extension conductor is adjusted so as to form a magnetic field in the Y direction. Specifically, the resonance frequency of the extension conductor is adjusted to be the same as the magnetic resonance frequency f0. Accordingly, for example, when receiving a signal of the third RF coil 410C, a current flows through the conductor 21C of the third RF coil 410C and a current also flows through the extension conductor 405 so as to form a magnetic field in the Y direction and hence a signal can be efficiently acquired. That is, the sensitivity is improved.

Further, the configuration of each sub-coil is the same as the configuration described for the sub-coil 410 of FIG. 5 in the embodiment of the MRI apparatus and the adjacent sub-coils are connected through the capacitor 425 so that the magnetic coupling is prevented. Further, the loop coil portion 420 of the sub-coil 410 and the low input impedance preamplifier 430 are connected to each other by the inductor 441 and the parallel resonance circuit is formed between the loop coil portion 420 and the low input impedance preamplifier 430. The parallel resonance circuit includes the parallel capacitor 424 inserted in series to the loop coil portion 420, the low input impedance preamplifier 430, the inductor 441, and the conductor portion connecting them and the impedance is formed so as to be higher than the impedance of other frequencies at f0. For example, the magnitude of the input impedance of the low input impedance preamplifier 430 is not limited, but for example, about 2Ω or less. Further, the resonance frequency of the parallel resonance circuit can be adjusted by adjusting the parallel capacitor 424, the inductor 441, and the inductor component of the conductor portion connecting them in consideration of these components. Furthermore, since the conductor portion also includes the inductor component, the inductor 441 is not essentially required and can be replaced by, for example, a capacitor.

In this way, when the frequency of the parallel resonance circuit between the loop coil unit 420 and the low input impedance preamplifier 430 is adjusted, it is possible to eliminate the magnetic coupling between the RF coils and to form the path of the extension conductor (FIG. 6). In this embodiment, as illustrated in FIG. 9, all sub-coils 410 of the first coil unit 401 have a configuration in which the parallel resonance circuit is formed at the top of the drawing of the path of the extension conductor and all sub-coils 410 of the second coil unit 402 have a configuration in which the parallel resonance circuit is formed at the bottom of the drawing. The lower conductor of the first coil unit 401, the capacitor 403-1 constituting the extension conductor control circuit 403, and the upper conductor of the second coil unit 402 constitute the extension conductor 405.

The extension conductor 405 is adjusted so as to resonate at the same frequency as the magnetic resonance frequency by adjusting the value of the capacitor 403-1 inserted into the extension conductor control circuit 403. The capacitor 426 which is inserted into the conductor portion 41 sharing the conductor with the extension conductor 405 while being inserted into each sub-coil 410 may be used to adjust the extension conductor 405.

Further, since the reactance of the extension conductor changes due to the magnetic coupling prevention means (in an example of FIG. 9, the capacitor 425) between the adjacent sub-coils, the resonance frequency of the extension conductor may be adjusted in consideration of the reactance. Furthermore, the magnetic coupling prevention means is not limited to the capacitor 425 and may be of, for example, a type using an inductor or an overlap type overlapping a part of patterns. In response to the type, the resonance frequency of the extension conductor is adjusted.

Next, an operation and an adjustment of each circuit element of the array coil 400 of this embodiment will be described. Here, in the MRI apparatus using the array coil 400 of this embodiment, the transmission RF coil is normally opened and a description of elimination of the magnetic coupling of the array coil 400, that is the reception RF coil, with the transmission RF coil is omitted.

The operation of the sub-coil is basically the same as the operation of the third RF coil 410C when supplying power in the embodiment of the MRI apparatus. That is, since the impedance of the parallel resonance circuit of each sub-coil is formed so as to be higher than the impedance of other frequencies at f0, as illustrated in FIG. 8(a), a shape in which the conductor 41C of the sub-coil 410C is connected to the extension conductor 405 is obtained. When viewed from the common portion 460C of the extension conductor and the conductor 41C of the sub-coil 410C, the extension conductor 405 can be regarded as a dipole antenna.

When supplying power to the sub-coil 410C, a loop current is first formed in the conductor 41C. Accordingly, since a potential difference occurs in the common portion 460C, the common portion can be regarded as a power supply point when viewed from the extension conductor. That is, power is supplied to the extension conductor so that the common portion 460C becomes a power supply point. In the dipole antenna, when viewed from the power supply point, one terminal has a positive potential and the other terminal has a negative potential, so that an electric field becomes higher at the ends . Then, when the extension conductor is disposed in a spiral shape, a potential difference occurs since the positive and negative ends are adjacent to each other and hence electric field coupling occurs. As a result, since the extension conductor which is disposed in a spiral shape causes a loop-shaped current through electric field coupling, the extension conductor can be regarded as a loop coil. Therefore, a loop-shaped current is also formed in the state of the dipole antenna. In the direction of the current generated at this time, since a current flows in the same direction in the common portion 460C, as illustrated in FIG. 8(b), the spiral extension conductor which generates a current like the figure of 8 together with the conductor 41C of the sub-RF coil 410C and is disposed on the XY plane generates a magnetic field in the Y direction, efficiently acquires a signal, and improves sensitivity.

Since the operation of the sub-coil other than the sub-coil 410C is the same and any sub-coil can operate the extension conductor as a part of each coil, even the RF coil having poor efficiency and disposed at a position where the depth sensitivity is not easily obtained can obtain high sensitivity by the extension conductor.

Further, in the description above, a capacitor 426C inserted into the common portion 460C is operated as a part adjusting the resonance frequency of the extension conductor 405, but the current flowing through the extension conductor can be controlled by changing the capacitor value to change the potential difference of the common portion. That is, the sub-coil which does not allow a current to flow through the extension conductor can be also formed. Since the sub-coil which is regarded such that the sub-coil is not electrically connected to the extension conductor can be provided in the coil unit, the degree of freedom in design is improved and the sensitivity can be improved.

With the above-described adjustment, each RF coil 410 can receive each nuclear magnetic resonance signal of a detection object.

When the array coil of this embodiment is disposed so that the body axis direction of the subject is disposed in a direction (Y direction) perpendicular to the static magnetic field direction (Z direction) in the vertical magnetic field type MRI apparatus, the array coil is disposed so as to cover the subject at least once so that the axial direction of the extension conductor becomes the Y direction as illustrated in FIG. 7(a). Further, in the arrangement in which the coil unit is connected to both sides of the extension conductor control circuit 403, as illustrated in FIG. 7(b), the sub-coils of the coil unit are displaced in the Y direction. Further, a configuration may be employed in which an overlapping portion of the sub-coils is connected in advance in an overlapping state and one end of the extension conductor control circuit 403 and the end of one coil unit are provided with a connection terminal and are connected through the connection terminal when attached to the subject.

ADJUSTMENT EXAMPLE 1

Hereinafter, the adjustment procedure of each circuit element of the array coil of this embodiment will be described in detail.

Here, an example in which the array coil 400 is adjusted to resonate at a magnetic resonance frequency of an atomic nucleus of hydrogen at a static magnetic field strength of 1.2 T (tesla) at 50 MHz (f0=50 MHz) will be described as an example.

As an example, the shape and the size of each sub-coil constituting the array coil are set such that the loop has a rectangular shape and the vertical and horizontal sizes of the loops of the respective sub-coils constituting the first coil unit 401 and the second coil unit 402 are 10 cm and 10 cm. Further, a capacitor is used as the magnetic coupling prevention means with the adjacent sub-coils. In this case, the vertical and horizontal sizes of each coil unit are 10 cm and 30 cm. The length of the extension conductor control circuit 403 connecting the coil unit is set to a length required for connecting both coil units when the array coil of this embodiment covers the subject at least once and the sub-coils of the first coil unit 401 and the second coil unit 402 are disposed in a partially overlapping state so as not to be magnetically coupled to each other.

Figure 10:
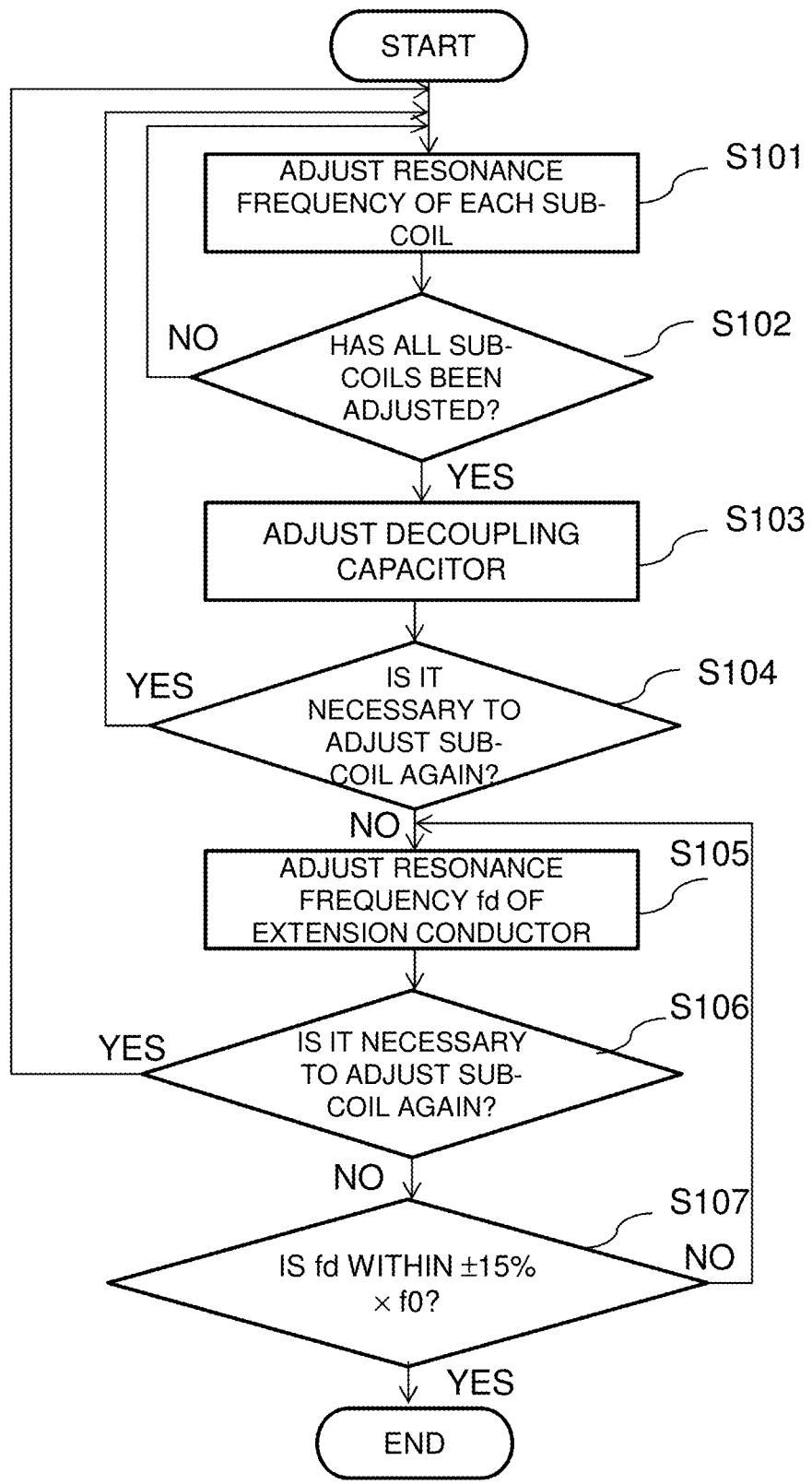
FIG. 10 is a diagram illustrating an example of a procedure of adjusting the array coil of the first embodiment.

Under such conditions of size and arrangement, the adjustment is performed in the following procedure. FIG. 10 illustrates an example of the procedure.

First, the first sub-coil 410A to the sixth sub-coil 410F are adjusted so as to be operated together at the magnetic resonance frequency (S101, S102). That is, in the impedance characteristic of the sub-coil when viewed from the input impedance preamplifier 430, the loop conductor of the sub-coil has a resonance peak at the magnetic resonance frequency and the impedance of the resonance peak is adjusted to 50Ω. Specifically, the series capacitor 422 and the capacitor 426 are adjusted to adjust the resonance frequency and the capacitor 424 is adjusted so that the input impedance of the circuit becomes 50Ω. Further, the parallel resonance circuit of the capacitor 424, the low input impedance preamplifier 430, and the inductor 441 when viewed from the capacitor 424 is adjusted to have high impedance.

Next, the decoupling capacitor 425 is adjusted so as to eliminate the magnetic coupling with the adjacent sub-coils of the array coil (S103). Additionally, when the resonance frequency and the input impedance of the sub-coil deviate due to the adjustment of the decoupling capacitor 425, the adjustment is appropriately performed again (S104).

Next, the resonance frequency (fd) of the extension conductor 405 is adjusted (S105). That is, the extension conductor is adjusted so as to resonate in the vicinity of the magnetic resonance frequency in the impedance characteristic of the sub-coil when viewed from the input impedance preamplifier 430. Specifically, the value of the capacitor 403-1 of the extension conductor control circuit 403 is adjusted to match the frequency higher than the magnetic resonance frequency by about 3%. Due to the frequency higher than the magnetic resonance frequency, a current of a figure of 8 is formed. When the input impedance and the resonance frequency of the sub-coil deviate due to the adjustment of the extension conductor control circuit 403, the adjustment is appropriately performed again as described above (S106). Here, the frequency is set to be higher by about 3%, because the resonance frequency (fd) of the extension conductor 405 is made to be higher than the magnetic resonance frequency even if there is a variation due to the subject, but the frequency is not limited thereto. Further, the resonance frequency (fd) of the extension conductor 405 is set to the frequency higher than the magnetic resonance frequency, but the invention is not limited thereto. When the adjustment is performed so as to resonate within ±15% of the magnetic resonance frequency, a current also flows to the extension conductor 405 so that a magnetic field is formed in the Y direction and a signal can be efficiently acquired (S107).

When the capacitors are adjusted in this procedure, each sub-coil 410 of the array coil 400 of this example resonates at a nuclear magnetic resonance frequency and receives a nuclear magnetic resonance signal. Further, each of the sub-coil 410A to the sub-coil 410F drives the spiral extension conductor 405 disposed to cover the subject. Since the axis of the spiral extension conductor 405 faces the Y direction perpendicular to the static magnetic field direction in the vertical magnetic field type MRI apparatus, the sensitivity of the array coil is improved even when the sub-coil 410 having an axis disposed in parallel to the static magnetic field direction is provided.

Figure 11:
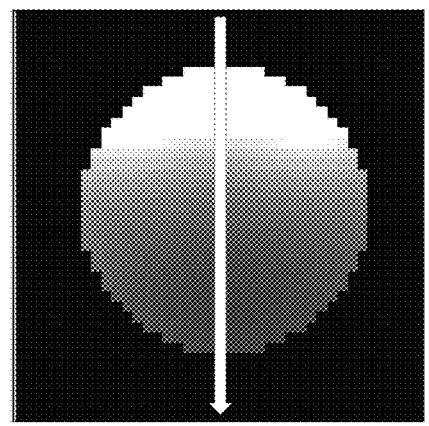
FIG. 11(a) is a graph of a sensitivity distribution of a coil of a related art.
FIG. 11(b) is a sensitivity distribution of the array coil of the first embodiment.
FIG. 11(c) is a graph of a sensitivity profile of coils of the related art and the first embodiment.
Figure 11:
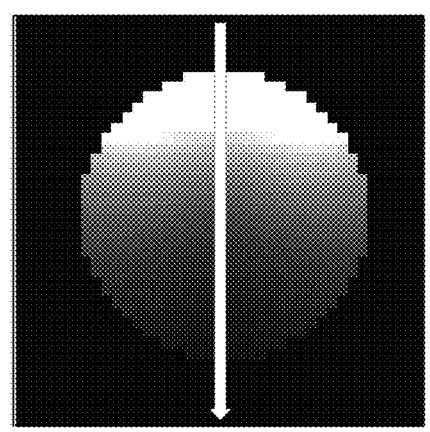
Figure 11:
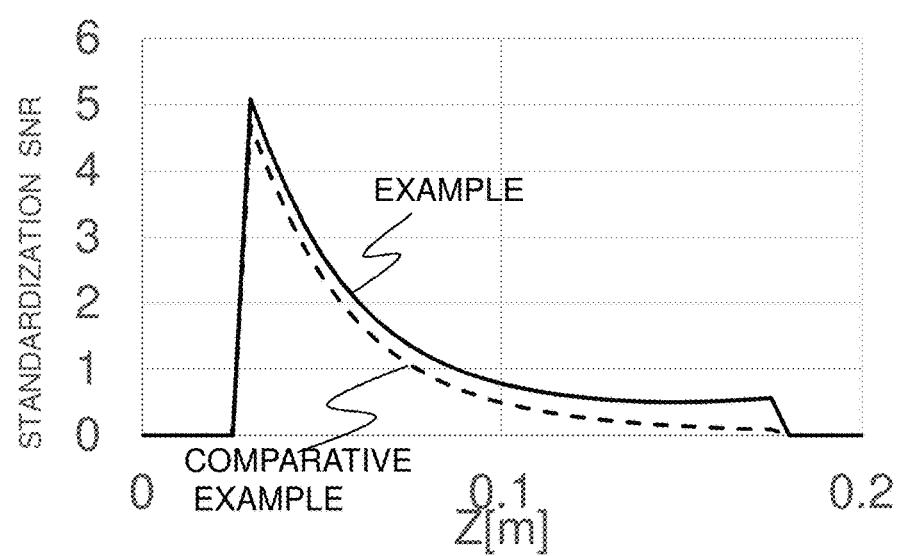

FIG. 11 illustrates a simulation result of imaging a water phantom with an MRI apparatus (1.2 Tesla, vertical magnetic field type) using the array coil adjusted as described above. FIG. 11(a) illustrates a sensitivity distribution of the third sub-coil 420C of this embodiment. FIG. 11(b) illustrates a sensitivity distribution of the conventional RF coil having the same shape. FIG. 11(c) shows a vertical line profile passing through the center of the phantom in FIGS. 11(a) and 11(b), where FIG. 11(a) is indicated by a solid line and FIG. 11(b) is indicated by a dotted line.

As understood from these results, in the array coil 400 of this example, the SNR in the deep part of the phantom is improved by using the spiral extension conductor.

Additionally, the numerical values and procedures illustrated in the above-described adjustment examples are examples. That is, the resonance frequency of each sub-coil and the resonance frequency of the extension conductor may be finally adjusted by a circuit element such as a capacitor. For example, the adjustment of the frequency of the extension conductor may be performed by the capacitor 426 inserted in series to the conductor 41 of each sub-coil instead of or together with the capacitor 403-1. Accordingly, the adjustment width of the resonance frequency of the extension conductor is widened and the degree of freedom is widened. However, when the resonance frequency of each RF coil shifts due to this, it is adjusted to guarantee with a capacitor other than the capacitor 403-1.

Additionally, the extension conductor of this embodiment is adjusted so as to resonate at a frequency higher than the magnetic resonance frequency and to allow the flow of a current of a figure of 8, the adjustment may be performed so that a current flows in a direction required for the extension conductor. In the resonance frequency within ±15%, a current flows through the extension conductor and hence high sensitivity can be obtained. As a result, the degree of freedom in optimizing the entire coil is widened, so that the design becomes easy and an optimized array coil unit can be realized.

<Modified Example of First Embodiment>

[Modified Example of Circuit Element]

Figure 12:
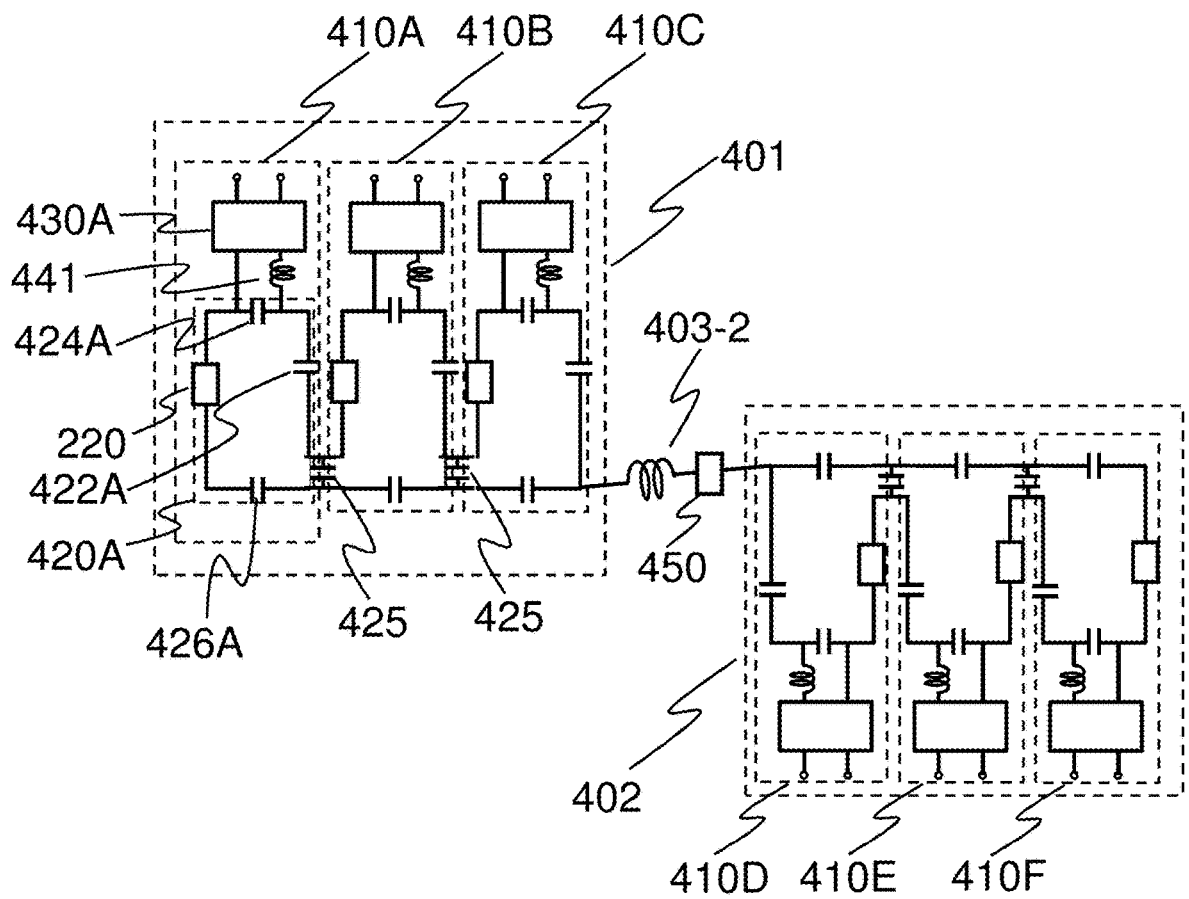
FIG. 12 is an explanatory diagram illustrating a configuration of an array coil 400 according to a modified example of the first embodiment.

In the first embodiment, the capacitor is disposed in the extension conductor control circuit 403, but the invention is not limited thereto. As illustrated in FIG. 12, an inductor 403-2 may be used in order to resonate the extension conductor at the magnetic resonance frequency. Further, the inductor 403-2 may not be the inductor element. By extending the conductor, the inductor component may be changed to resonate at the magnetic resonance frequency. Accordingly, since the resonance frequency adjustment range of the extension conductor is widened, an extension conductor suitable for the purpose can be formed and the sensitivity in the region of interest is improved.

Figure 13:
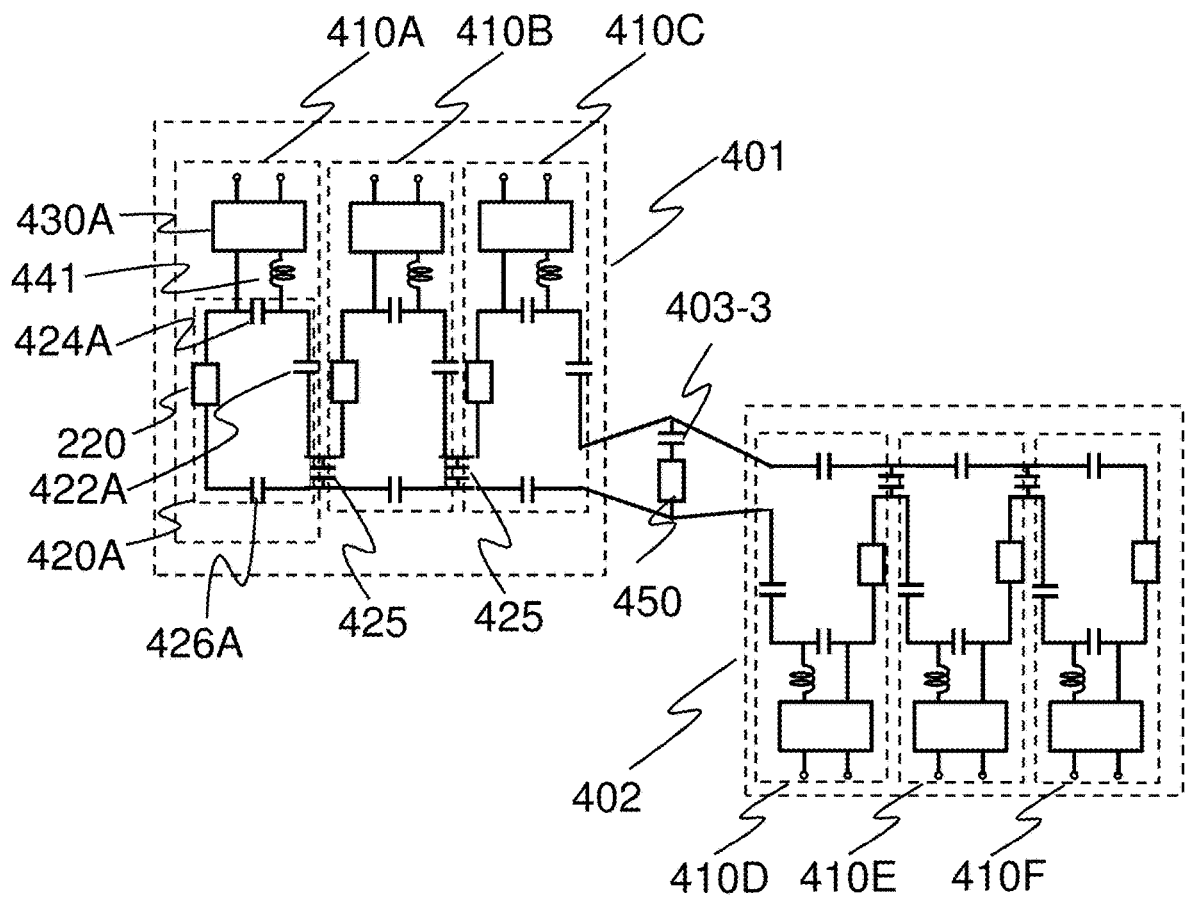
FIG. 13 is an explanatory diagram illustrating a configuration of the array coil 400 according to the modified example of the first embodiment.

Further, as the extension conductor control circuit 403, as illustrated in FIG. 13, a configuration may be adopted in which a capacitor 403-3 is inserted into a conductor of the sub-coil (here, the sub-coil 410C) located near the second coil unit in the first coil unit 401 and a conductor of the sub-coil (here, the sub-coil 410D) located near the first coil unit in the second coil unit 402 shares the capacitor 403-3. Accordingly, since the first coil unit 401 and the second coil unit 402 can be disposed adjacently while the magnetic coupling between the sub-coils is eliminated, the arrangement density of the coil is improved and the sensitivity is improved.

Figure 14:
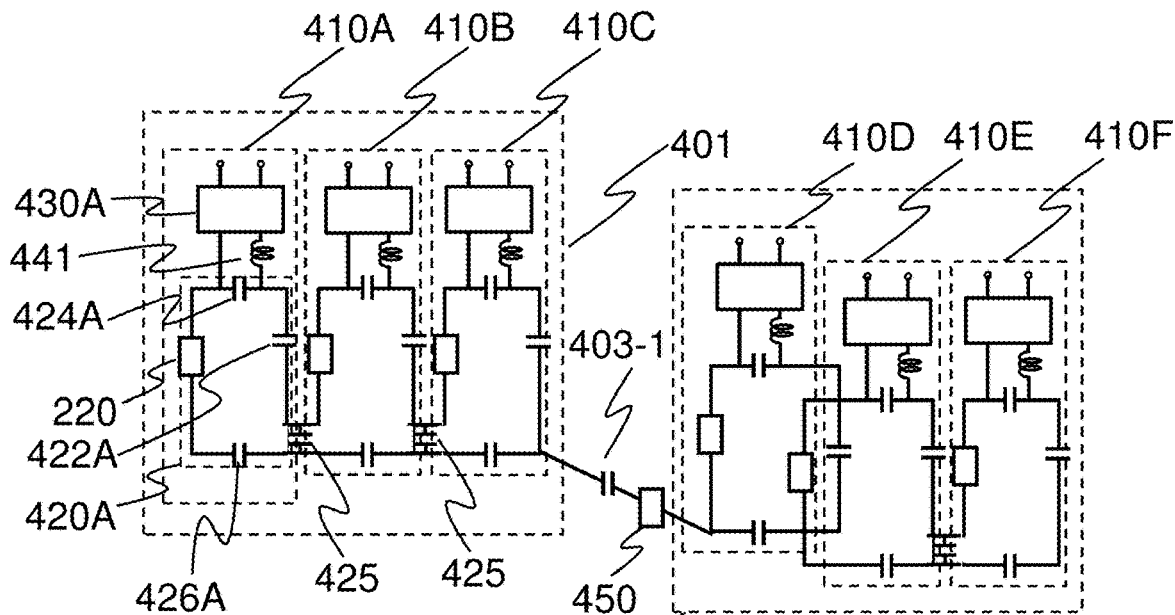
FIGS. 14(a) and 14(b) are respectively explanatory diagrams illustrating a configuration of the array coil 400 according to the modified example of the first embodiment.
Figure 14:
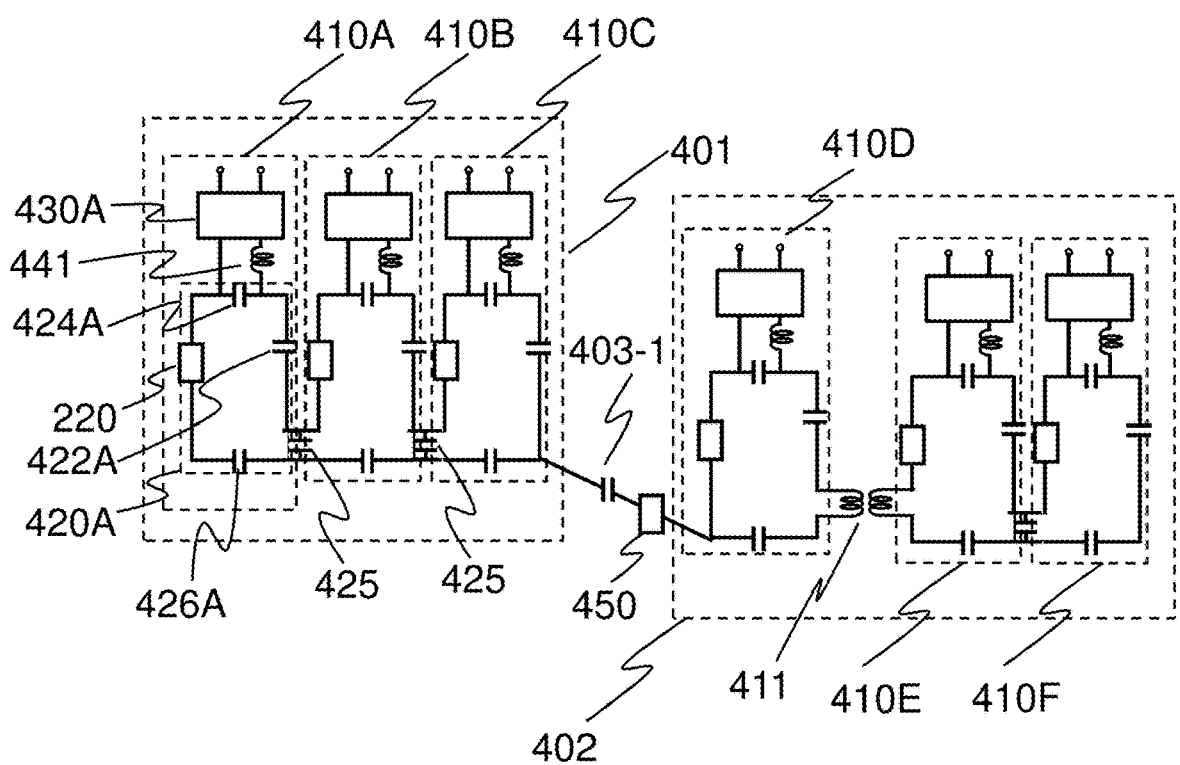

Further, in the first embodiment, the capacitor 425 is used as the magnetic coupling eliminating means between the adjacent sub-coils in each coil unit, but the invention is not limited thereto. For example, as illustrated in FIG. 14(a), an overlap type that eliminates the magnetic coupling by overlapping a part of coils may be used as in the fourth sub-coil 410D and the fifth sub-coil 410E. Further, as illustrated in FIG. 14(b), an inductor type that eliminates the magnetic coupling by adjusting the coupling coefficient between the inductors while inserting an inductor 411 into the coil conductor may be used as in the fourth sub-coil 410D and the fifth sub-coil 410E. Since the degree of freedom in designing the array coil is improved by using these, the coil can be designed according to the purpose and hence the final sensitivity can be improved.

Additionally, since the above-described types are used, the extension conductor includes a first extension conductor extending from the first sub-coil 410A to the fourth sub-coil 410D through the extension conductor control circuit 403 and a second extension conductor extending from the first sub-coil 410A to the sixth sub-coil 410F through the extension conductor control circuit 403 and the resonance frequency seen from each adjustment path is different. Accordingly, an arbitrary extension conductor can be formed by adjusting the resonance frequency of one to be operated as the extension conductor among the two to the magnetic resonance frequency.

[Modified Example of Structure and Sub-Coil]

Figure 15:
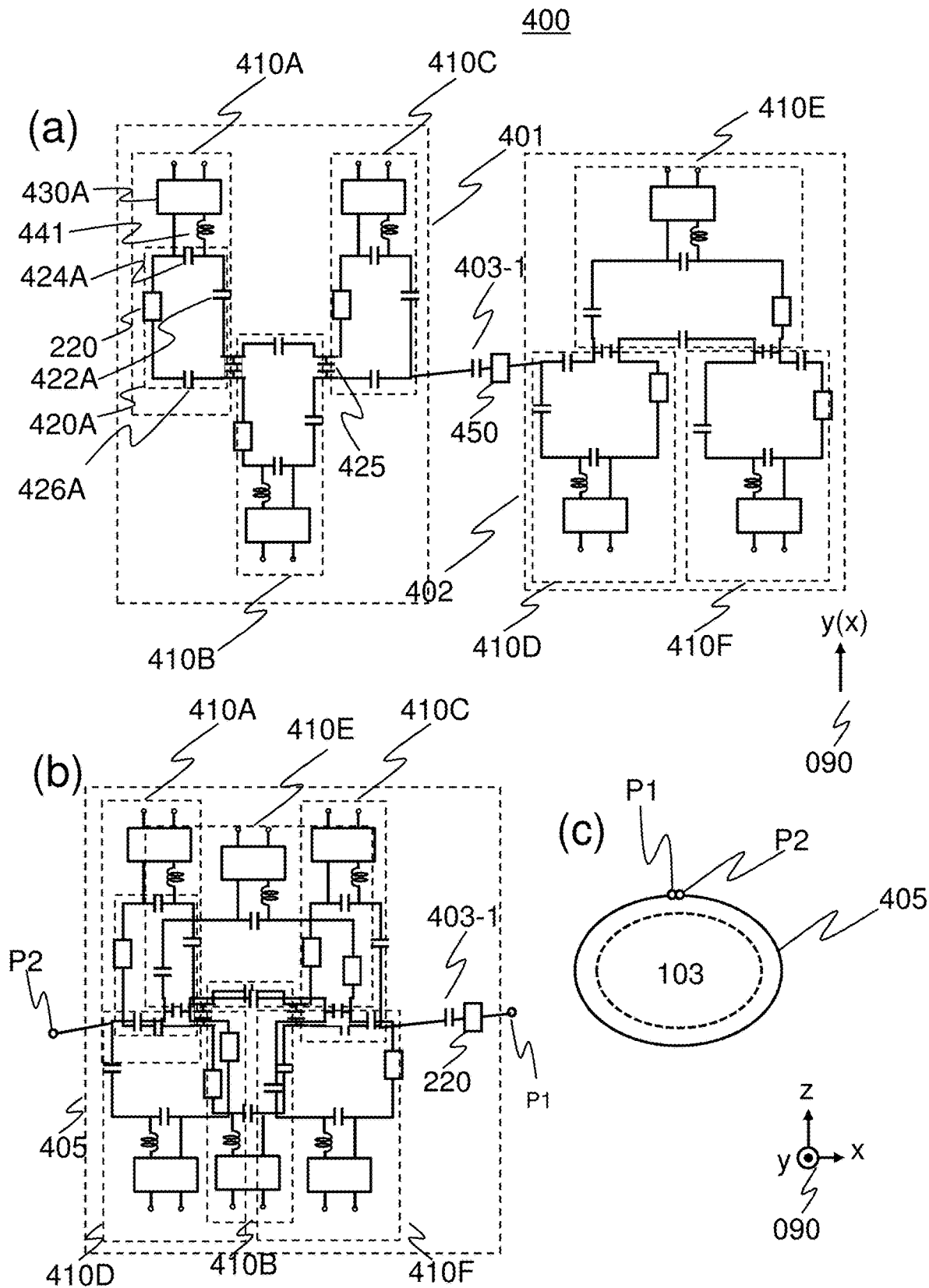
FIG. 15(a) is an explanatory diagram illustrating a configuration of the array coil 400 according to the modified example of the first embodiment.
FIG. 15(b) is a diagram illustrating an overlapping portion.
FIG. 15(c) is a diagram illustrating an arrangement example to a subject.

In the first embodiment, a case in which the extension conductor (the linear conductor) of the array coil 400 is substantially linear has been exemplified, but the invention is not limited thereto. For example, a wave shape maybe used. As illustrated in FIG. 15(a), a wave shape may be used by alternately changing the positions of the parallel capacitors 424 of the RF coils in the vertical direction. A current path can be formed according to the necessity. Accordingly, the degree of freedom in designing the sensitivity distribution generated by the linear conductors is widened and the sensitivity suitable for the purpose can be obtained, so that the sensitivity is improved. Also, the degree of freedom in adjusting the resonance frequency of the linear conductor is widened.

Further, when the coils are disposed vertically in the array coil in this way, a combination configuration can be used such that the sub-coil of the other coil unit is disposed at a position where the sub-coil of one coil unit is absent when the coils are disposed to cover the subject. As a result, since the degree of freedom in coil design is increased, the coil can be designed in accordance with the purpose and hence the final sensitivity can be improved.

FIG. 15(b) is a diagram illustrating a modified example of a case in which a portion covering the array coil at least once is overlapped in advance. A solid line indicates the first coil unit 401 and a dashed line indicates the second coil unit 402. The extension conductor control circuit 403 is connected to the third sub-coil 410C and is connected to a terminal P1. Further, a terminal P2 is connected to the fourth sub-coil 410D. When the terminals P1 and P2 are connected so as to cover the subject, the configuration is the same as that the coil unit is disposed on both sides of the extension conductor control circuit 403, and hence the same effect can be obtained. Further, in this configuration, as illustrated in FIG. 15(c), the array coil only needs to be wound around the subject once, so that the handling of the array coil is facilitated.

Furthermore, an example in which each coil unit of the first embodiment includes three sub-coils has been described, but the invention is not limited thereto. The number of the sub-coils may be one, two, or four or more. Further, the number of the sub-coils constituting the coil unit may not be equal and may be different in the plurality of coil units constituting the array coil. Furthermore, a case in which the number of the coil units is two is illustrated in the drawing, but the number of the coil units may be increased. Accordingly, it is possible to design an array coil having an optimal number of channels according to the number of channels of the receiver and thus to improve the sensitivity.

Second Embodiment

In the first embodiment, the array coil including the first coil unit 401, the second coil unit 402, and the extension conductor control circuit 403 has been described, but the array coil of this embodiment is obtained by further adding a third coil unit 404 to the array coil of the first embodiment.

Figure 16:
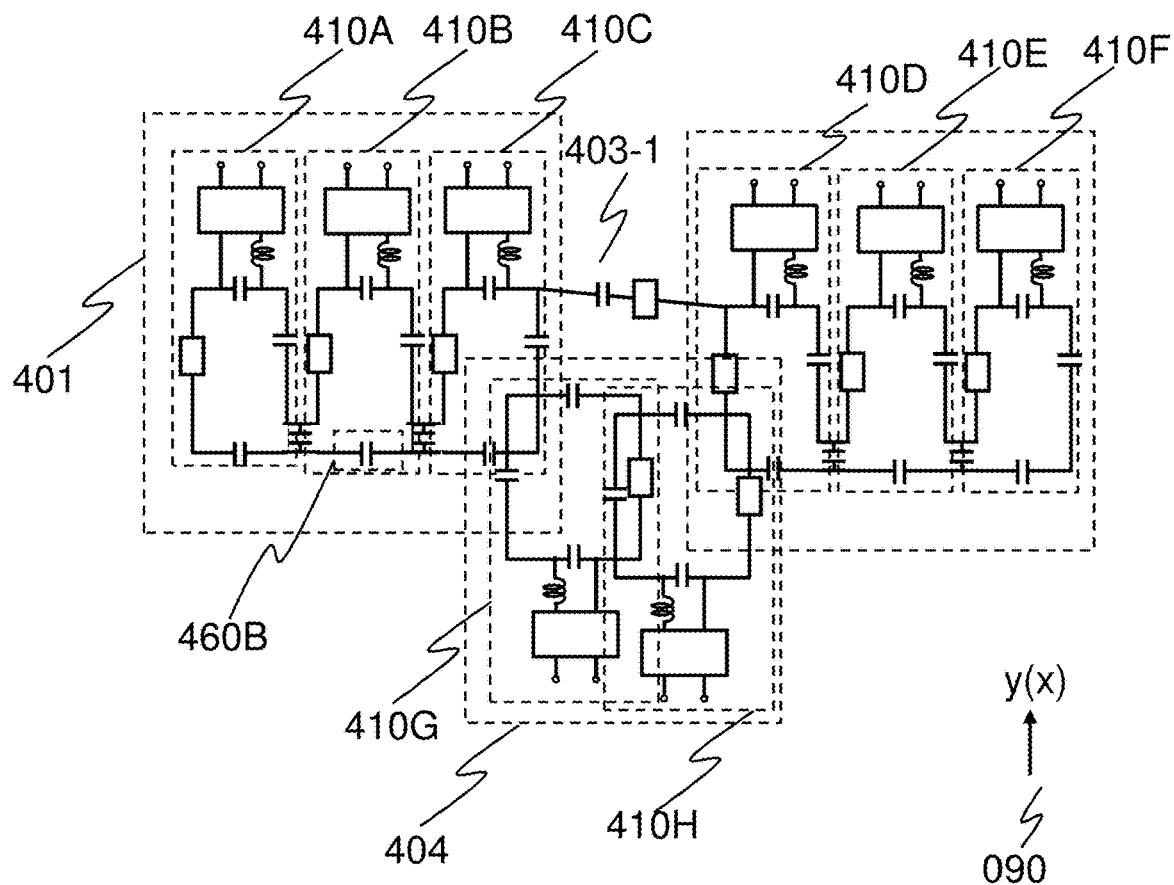
FIG. 16(a) is a diagram illustrating a circuit for illustrating a configuration of an array coil according to a second embodiment and FIG. 16(b) is a diagram illustrating an arrangement example to a subject.
Figure 16:
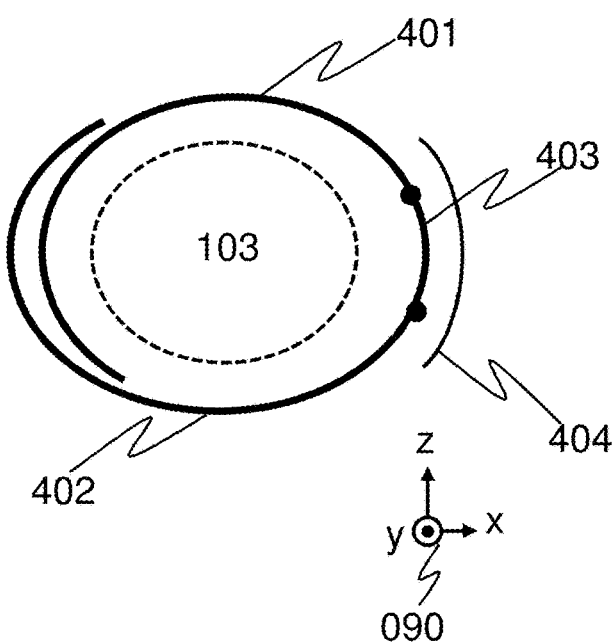

FIG. 16 is a diagram illustrating an array coil 500 of this embodiment. The first coil unit 401, the second coil unit 402, and the extension conductor control circuit 403 are basically adjusted similarly to the first embodiment and perform the same operation. That is, the nuclear magnetic resonance signal is detected by each of the sub-coils and the extension conductor sharing a part of the conductor with them. In this embodiment, as illustrated in FIG. 16(a), the third coil unit 404 is further disposed between the first coil unit 401 and the second coil unit 402. The coil unit 404 includes one or more sub-coils. In the example illustrated in the drawing, the coil unit includes two sub-coils of a seventh sub-coil 410G and an eighth sub-coil 410H.

In each of the sub-coil 410G and the sub-coil 410H, an adjustment circuit such as a capacitor connected in series to the loop coil unit and the conductor constituting the loop coil unit is inserted and the sub-coil is adjusted so as to resonate at the same frequency as the magnetic resonance frequency f0 in order to acquire the magnetic resonance signal similarly to each sub-coil 410 of the first embodiment. Further, the magnetic coupling between the sub-coil 410G and the sub-coil 410H is eliminated by the overlap type magnetic coupling prevention means so as not to be magnetically coupled to each other. Similarly, the magnetic coupling between the sub-coil 410C and the sub-coil 410G of the first coil unit and the sub-coil 410D and the sub-coil 410H of the second coil unit is eliminated by the overlap type magnetic coupling prevention means so as not to be magnetically coupled to each other.

Similarly to the array coil 400 of the first embodiment, as illustrated in FIG. 16(b), the array coil 400 of this embodiment is disposed with respect to the subject such that the subject 103 is covered at least once, the axis of the extension conductor 405 is in the Y direction (a direction perpendicular to the static magnetic field direction), and the extension conductor 405 has a spiral shape. Further, in the case of the vertical magnetic field type MRI apparatus, for example, the sub-coil constituting the third coil unit 404 is disposed so as to be located on the side surface of the subject 103.

Next, an operation of the array coil 500 with the above-described configuration will be described.

In the array coil 500 of this embodiment, since the first coil unit 401, the extension conductor control circuit 403, and the second coil unit 402 are basically the same as those of the array coil 400 of the first embodiment and the basic principle or adjustment method is the same as that of the first embodiment, the operation of the added third coil unit will be described. In the following description, for the simple description, the description will be made with the operation at the time of power supply on the basis of the reciprocity theorem that the operation and sensitivity at the time of reception of the RF coil are the same as the operation and sensitivity at the time of power supply to the coil.

When power is supplied to the sub-coil 410G of this embodiment, it is hardly magnetically coupled with the sub-coil 410H and the sub-coil 410C since an overlap type magnetic coupling prevention means is configured in addition to a preamplifier decoupler including the capacitor 424, the low input impedance preamplifier 430, and the inductor 441. However, since the magnetic coupling prevention means is provided only in the preamplifier decoupler with regard to other RF coils, some magnetic coupling may occur.

For example, when power is supplied to the sub-coil 410G, magnetic coupling with the sub-coil 410B occurs. As a result, almost no current flows in the periphery of the capacitor 424 of the sub-coil 410 due to the preamplifier decoupler, but a current flows in other areas. Accordingly, since a potential difference occurs in the common portion 460B between the sub-coil 410B and the extension conductor 405, the common portion is operated like a power supply point when viewed from the extension conductor. Thus, a current also flows to the extension conductor and similarly to the first embodiment, the extension conductor 405 forms a loop current and generates a magnetic field in the Y direction. As a result, depth sensitivity can be obtained.

Further, when power is supplied to the sub-coil 410G, magnetic coupling occurs in the first sub-coil 410A and the sub-coils 410D, 410E, and 410F of the second coil unit as well as the sub-coil 410B. Accordingly, a current flows through the extension conductor and constitutes the sensitivity. As a result, the sensitivity is improved.

The same applies to the other sub-coils constituting the third coil unit, that is, the sub-coil 410H.

In this way, in the array coil 500 of this embodiment, even when the sub-coil does not constitute the extension conductor, it is not possible to improve the sensitivity by contributing to the sensitivity of the extension conductor by coupling with the sub-coil constituting the extension conductor. Thus, FIG. 16(b) illustrates a case in which the third coil unit 404 is disposed on the side surface of the subject, but the effect of improving the sensitivity can be obtained while the arrangement position is not limited. Accordingly, the degree of freedom in the arrangement of the third array coil is increased.

Further, in this embodiment, a case in which the third coil unit 404 includes two sub-coils has been described as an example, but the invention is not limited thereto. The number of sub-coils may be one or three or more. Since the degree of freedom in the number of the channels of the RF coil is widened, the array coil can be designed with high sensitivity.

According to this embodiment, since the third coil unit is disposed in parallel to the extension conductor control circuit 403 inserted between the coil units, the extension conductor control circuit 403 can prevent the arrangement density of the sub-coils from becoming sparse and increase the sensitivity. Further, the sub-coil constituting the third coil unit in parallel to the extension conductor control circuit 403 can contribute to the improvement of the sensitivity of the extension conductor.

Third Embodiment

In the first embodiment, the array coil including the first coil unit 401, the second coil unit 402, and the extension conductor control circuit 403 has been described, but the array coil of this embodiment has a configuration in which an RF coil is added between the adjacent coil units and the extension conductor control circuit shares a part of the added RF coil.

Figure 17:
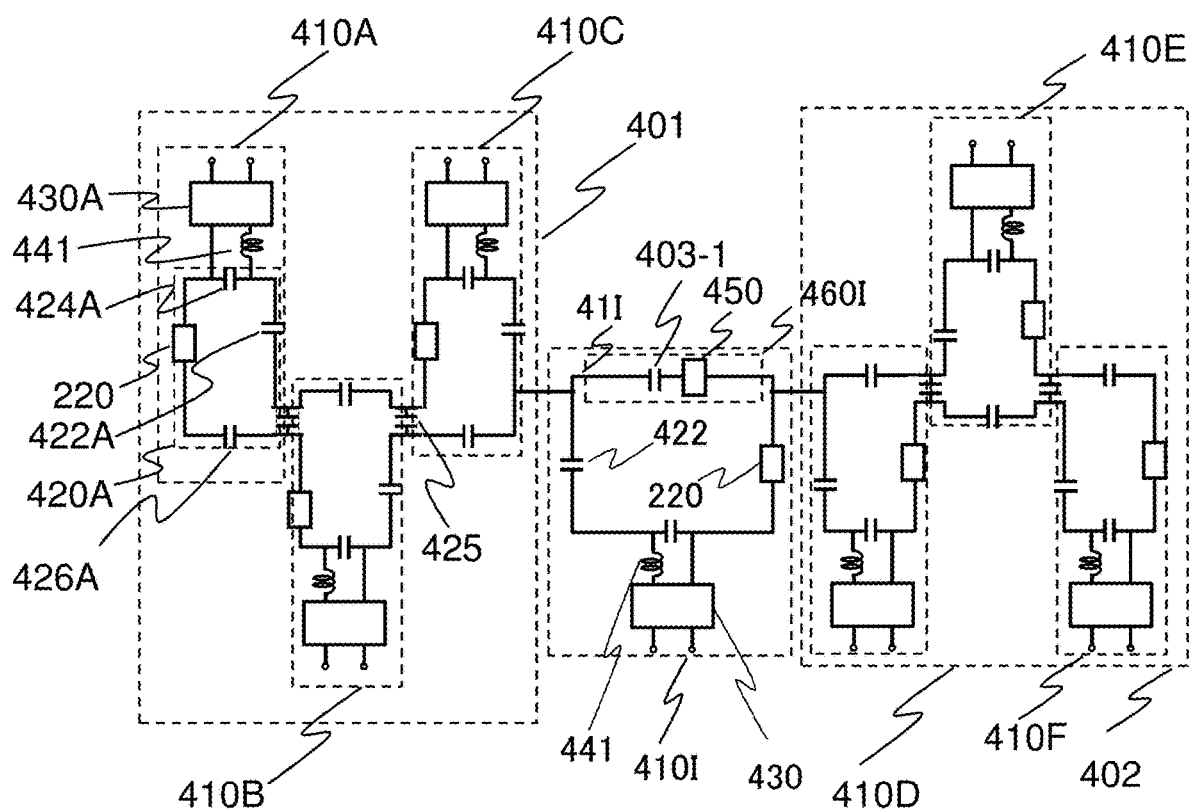
FIG. 17 is a diagram illustrating a circuit for illustrating a configuration of an array coil according to a third embodiment.

FIG. 17 is a diagram illustrating an array coil 600 of this embodiment. Here, the first coil unit 401 and the second coil unit 402 basically have the same configuration as that of the modified example of the first embodiment (FIG. 16), but may adopt the configuration illustrated in FIG. 9 or the configuration of other modified examples.

In this embodiment, a seventh sub-coil 410I is provided in addition to the first coil unit 401 and the second coil unit 402 and a part of the conductor 41I is formed as the extension conductor control circuit 403.

The adjustment of the array coil 600 of this embodiment is performed, for example, as below. First, the first coil unit 401 and the second coil unit 402 are adjusted similarly to the array coil 400 due to the configuration similar to the array coil 400 illustrated in FIG. 16. Next, the seventh sub-coil 410I is formed such that the capacitor 403-1 and the magnetic coupling prevention circuit 220 are a part of the conductor 41I. The configuration of the sub-coil 410I is the same as those of the other sub-coils 410 except that a part of the conductor 41 is further provided with the capacitor 403-1 and the magnetic coupling prevention circuit 220. Further, since the adjustment circuit element such as the parallel capacitor 424 and the series capacitor 422 is provided and the magnetic resonance signal is acquired similarly to each sub-coil 410, the sub-coil is adjusted so as to resonate at the same frequency as the magnetic resonance frequency f0. Further, the extension conductor is also adjusted similarly to the first example and is disposed so as to cover the subject.

Next, an operation of the array coil 600 of this embodiment will be described.

In the array coil 600 of this embodiment, since the operation and the adjustment method of the first coil unit 401, the extension conductor control circuit 403, and the second coil unit 402 are basically the same as those of the first embodiment, the operation of the added seventh sub-coil 410I will be described.

Further, in the following description, for the simple description, the description will be made with the operation at the time of power supply on the basis of the reciprocity theorem that the operation and sensitivity at the time of reception of the RF coil are the same as the operation and sensitivity at the time of power supply to the coil.

First, the sub-coil 410I is also adjusted so that the impedance of the parallel resonance circuit including the parallel capacitor 424, the low input impedance preamplifier 430, and the inductor 441 becomes higher than the impedance of other frequencies at f0. For that reason, when viewed from the sub-coil 410I, the parallel resonance circuit from the first sub-coil 410A to the sixth sub-coil 410F is opened. That is, the conductor 41I of the sub-coil 410I is connected to the extension conductor 405. Then, when viewed from a common portion 460I between the extension conductor 405 and the conductor 41I of the sub-coil 410I, the extension conductor can be regarded as a dipole antenna.

Accordingly, when power is supplied to the sub-coil 410I, a loop current is first formed in the conductor 41I. Accordingly, since a potential difference occurs in the common portion 460I, the common portion can be regarded as a power supply point when viewed from the extension conductor 405. That is, the common portion 460I becomes a power supply point and supplies power to the extension conductor 405. Since the extension conductor 405 is disposed in a spiral shape and the end is disposed at a close position, electric field coupling occurs at that position. As a result, the extension conductor 405 forms a loop-shaped current in a state of a dipole antenna. In the direction of the current generated at that time, since a current flows in the same direction in the common portion 460I, the spiral extension conductor which generates a current like the figure of 8 together with the conductor 41I of the sub-coil 410I and is disposed on the XY plane generates a magnetic field in the Y direction, efficiently acquires a signal, and improves sensitivity.

According to this embodiment, since a part of the sub-coil in which the added extension conductor control circuit is inserted between the coil units is shared, the extension conductor control circuit 403 can prevent the arrangement density of the sub-coils from becoming sparse and increase the sensitivity similarly to the second embodiment. Further, the sensitivity is improved by further adding an optimum coil in the magnetic field direction.

<Modified Example of Third Embodiment>

Figure 18:
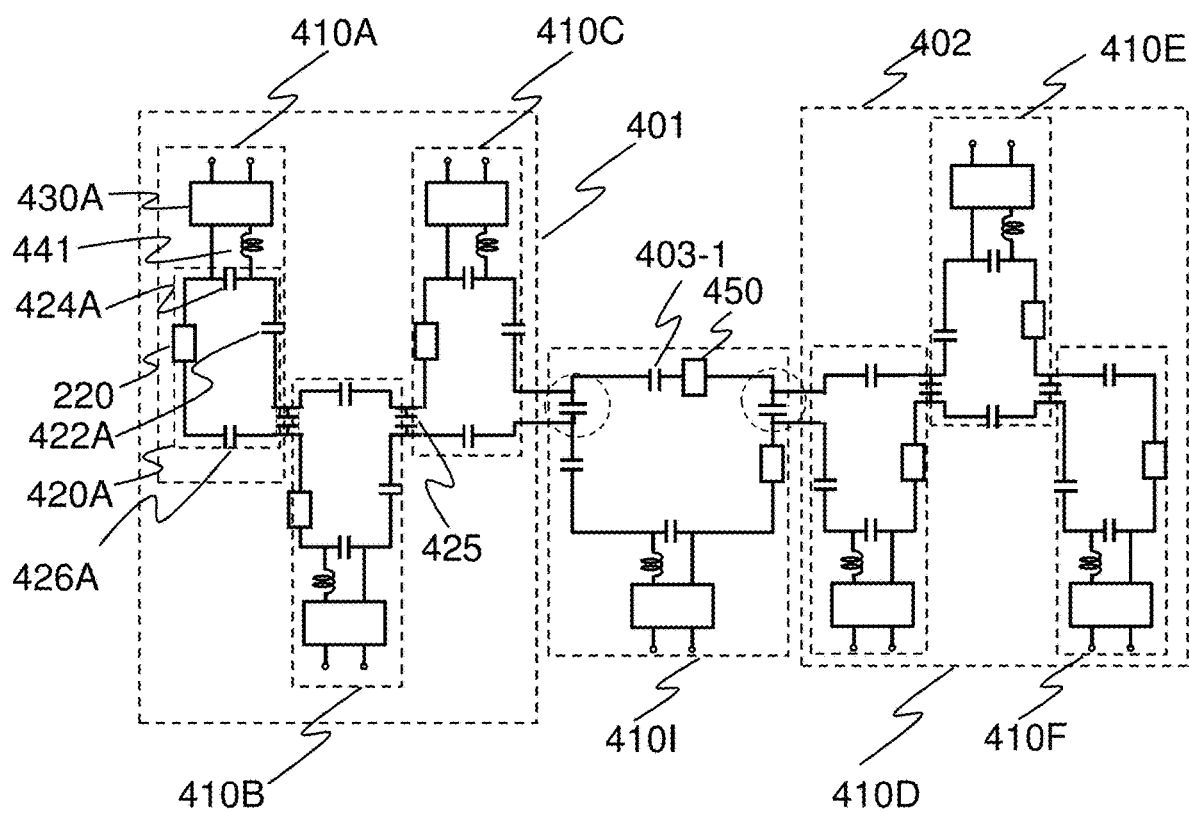
FIG. 18 is an explanatory diagram illustrating a configuration of an array coil according to a modified example of the third embodiment.

In the array coil illustrated in FIG. 17, a case is illustrated in which the preamplifier de-coupling consisting of the capacitor 424, the low input impedance preamplifier 430, and the inductor 441 is provided as the magnetic coupling prevention means of the sub-coil 410I, but the invention is not limited thereto. For example, as indicated by a circle surrounded by a dotted line in FIG. 18, magnetic coupling with an adjacent coil may be eliminated by a method using a capacitor or an overlap method or a method using an inductor maybe used.

Figure 19:
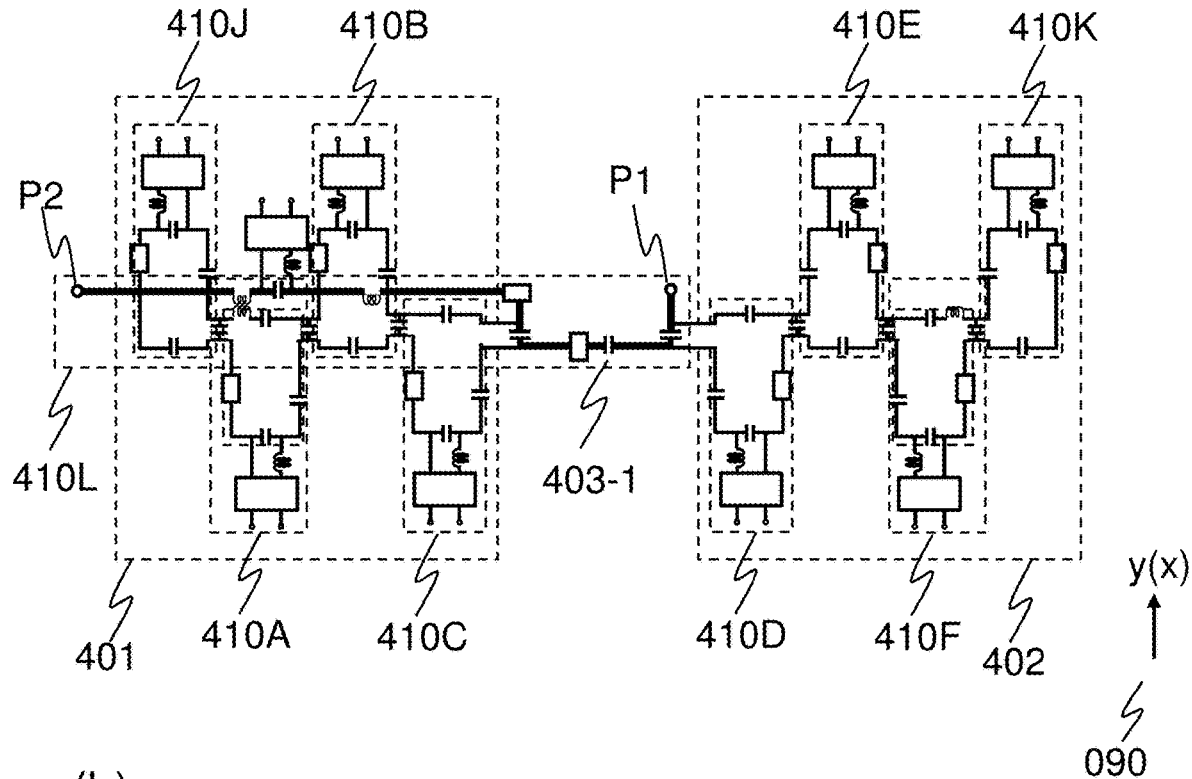
FIG. 19(a) is an explanatory diagram illustrating a configuration of the array coil according to the modified example of the third embodiment and FIG. 19(b) is a diagram illustrating an arrangement example to a subject.
Figure 19:
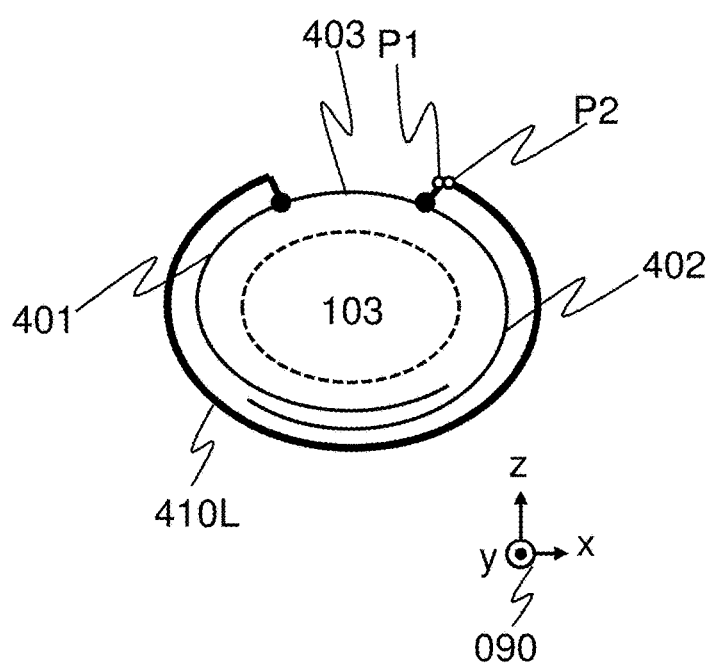

Further, in the third embodiment, the sub-coil including the extension conductor control circuit is the surface coil, but the invention is not limited thereto. For example, a solenoid coil may be used. An example in which the solenoid coil is used as the sub-coil is illustrated in FIG. 19(a). In this array coil 700, the first coil unit 401 and the second coil unit 402 respectively include four sub-coils 410A to 410C and the sub-coils 410J, 410D to 410F, and 410K and the extension conductor control circuit 403 is disposed between the coil units 401 and 402. In the drawing, a part (common portion) of the conductor from the sub-coil 410J of the left end to the sub-coil 410K of the right end shares the conductor with the extension conductor 405.

Further, one end of the extension conductor control circuit 403 (403-1) is provided, through a capacitor, with the terminal P1 provided serving as a means for eliminating the magnetic coupling with the adjacent sub-coil, that is, the sub-coil 410D, and the other end thereof is connected, through the same capacitor, with a coil conductor provided with the terminal P2 connected to the terminal P1. By connecting the terminal P1 and the terminal P2, as illustrated in FIG. 19(b), a sub-coil 410L having a solenoid coil shape wound around the subject 103 is obtained. In a state in which the terminal P1 and the terminal P2 are connected, a surface coil array of two rows and four columns is also formed by the sub-coils of the coil unit. A magnetic coupling eliminating means is appropriately provided between the solenoid coil 410L and a sub-coil at a position overlapping thereto. In an example illustrated in FIG. 19(a), as the magnetic coupling eliminating means, an inductor is inserted into each conductor loop of the sub-coil 410A and the solenoid coil 410L so as to adjust the mutual inductance and to prevent magnetic coupling.

Since the adjustment method and the operation of the array coil 700 of this embodiment are basically the same as those of the third embodiment, the description will be omitted.

According to the modified example, the sensitivity is improved by further adding the optimum coil in the direction of the magnetic field and further adding the surface coil.

Furthermore, also in the third embodiment and the modified example, the configurations of the second embodiment or the respective modified examples described in the first embodiment can be adopted individually or in combination as appropriate. For example, the adjustment circuit element or the inductor can be appropriately modified or the third coil unit 404 which does not directly share the conductor with the extension conductor can be added similarly to the array coil of the second embodiment. The sensitivity is further improved by increasing the number of RF coils.

As described above, according to the array coil of the above-described embodiments, it is possible to achieve multi-channel, high efficiency, and high sensitivity at the same time. Further, the multi-channel and high efficiency can be realized by adjusting the arrangement and the value of the circuit element. Thus, the configuration is not complicated.

However, the invention is not limited to these embodiments and can be modified appropriately such that the components are added or deleted or the embodiments are combined.

REFERENCE SIGNS LIST

090 Coordinate system
100 MRI apparatus

101 MRI apparatus
102 Table
103 Inspection target
110 Magnet
111 Magnet
121 SIMM coil
122 SIMM power supply
131 Gradient magnetic field coil
132 Gradient magnetic field power supply
140 Sequencer
151 Transmission RF coil
152 RF magnetic field generator
161 Reception RF coil
162 Receiver
170 Computer
171 Display device
180 Magnetic coupling prevention circuit driving device
210 Transmission/reception magnetic coupling prevention circuit
211 PIN diode
212 Control signal line
220 Transmission/reception magnetic coupling prevention circuit
221 PIN diode
221 Cross diode
222 Inductor
223 Control signal line
300 Umbrella-shaped RF coil
301 Linear conductor
302 End conductor
303 Capacitor
311 Input port
312 Input port
400 Array coil
401 First coil unit
402 Second coil unit
403 Extension conductor control circuit
403-1 Capacitor
405 Extension conductor
410 Sub-coil
41 Conductor
420 Loop coil unit
421 Loop
422 Series capacitor
424 Parallel capacitor
430 Low input impedance preamplifier
441 Inductor
450 Transmission/reception magnetic coupling prevention circuit
460 Common portion
500 Array coil
600 Array coil
700 Array coil

The invention claimed is:

1. A high-frequency array coil comprising:
a first coil unit having a plurality of sub-coils, each of which includes an RF reception coil including a conductor loop and is adjusted to receive a magnetic resonance signal;
a second coil unit having a plurality of sub-coils, each of which includes an RF reception coil including a conductor loop and is adjusted to receive the magnetic resonance signal;
an extension conductor control circuit interposed between and connected to the first coil unit and the second coil unit; and
an extension conductor which includes a linear conductor portion that connects a part of each of the conductor loops of the first coil unit and the second coil unit,
wherein the extension conductor control circuit adjusts a reception frequency of the extension conductor.

2. The high-frequency array coil according to claim 1, wherein a direction of a main magnetic field detected by the extension conductor intersects a direction of a main magnetic field detected by each of the plurality of RF reception coils.

3. The high-frequency array coil according to claim 1, wherein the extension conductor is wound in a spiral shape.

4. The high-frequency array coil according to claim 1, wherein a part of the plurality of RF reception coils of each of the first and second coil units overlap each other in an end of the extension conductor so that loop surfaces of the conductor loops are parallel to each other.

5. The high-frequency array coil according to claim 1, wherein in the extension conductor control circuit, an end connected to the extension conductor on the side of the first coil unit is also connected to the conductor loop of the RF reception coil adjacent to the extension conductor control circuit among the plurality of RF reception coils constituting the second coil unit and an end connected to the extension conductor on the side of the second coil unit is also connected to the conductor loop of the RF reception coil adjacent to the extension conductor control circuit among the plurality of RF reception coils constituting the first coil unit.

6. The high-frequency array coil according to claim 1, wherein a third coil unit including one or a plurality of RF reception coils is connected between the first coil unit and the second coil unit.

7. The high-frequency array coil according to claim 6, wherein the third coil unit is disposed in parallel to the extension conductor control circuit while preventing magnetic coupling with the RF reception coil of the first coil unit and the RF reception coil of the second coil unit.

8. The high-frequency array coil according to claim 6, wherein the third coil unit includes an RF reception coil which includes the extension conductor control circuit in the conductor loop.

9. The high-frequency array coil according to claim 1, wherein the extension conductor control circuit includes a capacitor or an inductor.

10. The high-frequency array coil according to claim 1, wherein each conductor loop of the RF reception coil includes a circuit element which adjusts a reception frequency of the RF reception coil and a part of the circuit element serves as the extension conductor control circuit.

11. The high-frequency array coil according to claim 1, wherein the reception frequency of the extension conductor is adjusted within ±15% of a frequency of the magnetic resonance signal by the extension conductor control circuit.

12. The high-frequency array coil according to claim 1, wherein in at least one of the first and second coil units, one or a plurality of RF reception coils among the plurality of RF reception coils are RF reception coils which are connected to the RF reception coils other than the one or the plurality of RF reception coils via a magnetic coupling prevention means.

13. The high-frequency array coil according to claim 1, further comprising:
 a loop coil which passes through the extension conductor control circuit and is parallel to the extension conductor.

14. A magnetic resonance imaging apparatus comprising:
 a static magnetic field generating magnet which generates a static magnetic field in a vertical direction;
 a gradient magnetic field generating coil which applies a magnetic field gradient to the static magnetic field; and
 a high-frequency coil which generates a high-frequency magnetic field in a space of a static magnetic field generated by the static magnetic field generating magnet or detects the high-frequency magnetic field,
 wherein the high-frequency coil is the high-frequency array coil according to claim 1.

* * * * *